United States Patent
Minami et al.

(10) Patent No.: US 6,511,997 B1
(45) Date of Patent: Jan. 28, 2003

(54) AMINOPYRAZOLE DERIVATIVES

(75) Inventors: Nobuyoshi Minami, Yokohama (JP); Michitaka Sato, Kawasaki (JP); Koichi Hasumi, Machida (JP); Norio Yamamoto, Kawasaki (JP); Katsuyuki Keino, Yokohama (JP); Teruaki Matsui, Kawasaki (JP); Arihiro Kanada, Kawasaki (JP); Shuji Ohta, Kawasaki (JP); Takahisa Saito, Kawasaki (JP); Shuichiro Sato, Kawasaki (JP); Akira Asagarasu, Machida (JP); Satoshi Doi, Kawasaki (JP); Motohiro Kobayashi, Kawasaki (JP); Jun Sato, Kawasaki (JP); Hajime Asano, Kawasaki (JP)

(73) Assignee: Teikoku Hormone Mfg. Co., Ltd., Tokyo (JP)

( * ) Notice: Subject to any disclaimer, the term of this patent is extended or adjusted under 35 U.S.C. 154(b) by 0 days.

(21) Appl. No.: 09/869,051

(22) PCT Filed: Dec. 21, 1999

(86) PCT No.: PCT/JP99/07186

§ 371 (c)(1),
(2), (4) Date: Jun. 22, 2001

(87) PCT Pub. No.: WO00/39116

PCT Pub. Date: Jul. 6, 2000

(30) Foreign Application Priority Data

Dec. 25, 1998 (JP) .................................... 10-371094

(51) Int. Cl.[7] ................ A61K 31/4409; A61K 31/4439; C07D 401/04

(52) U.S. Cl. ................... 514/341; 514/255; 546/268.4; 546/275.4

(58) Field of Search .......................... 514/235.5, 237.2, 514/255, 341; 546/268.4, 275.4

(56) References Cited

U.S. PATENT DOCUMENTS 5,932,576 A * 8/1999 Anantanarayan et al. 514/235.5
6,087,496 A * 7/2000 Anatanarayan et al. ..... 544/124

FOREIGN PATENT DOCUMENTS

| EP | 0846686 | 6/1998 |
| WO | 95/15318 | 6/1995 |
| WO | 96/03385 | 2/1996 |
| WO | 98/52937 A2 | 11/1998 |
| WO | 98/52937 | * 11/1998 |
| WO | 98/52940 A1 | 11/1998 |
| WO | 98/52940 | * 11/1998 |
| WO | 98/52941 | 11/1998 |
| WO | 98/56377 | 12/1998 |
| WO | 99/58523 | 11/1999 |

OTHER PUBLICATIONS

English Abstract WO 9852940, Anantanarayan et al Nov. 26, 1998 RN# 216504–38–0.*
Patent Abstracts of Japan, vol. 0172, No.91 (c–1067), Jun. 4, 1993 and JP 05 017470 A, Jan. 26, 1993.
Keith P. Wilson et al.: "The structural basis for the specificity of pyridinylimidazole inhibitors of p38 MAP kinase" Chemistry and Biology, vol. 4, No. 6, 1997, pp. 423–431.
Stephen E. De Laszlo et al.: "Pyrroles and other Heterocycles as inhibitors of p38 Kinase" Biorganic & Medicinal Chemistry Letters, No. 8, 1998, pp. 2689–2694.
Timothy F. Gallagher: "Regulation of Stress–induced Cytokine production of Pyridinylimidazoles; Inhibition of CSBP Kinase" Biorganic & Medicinal Chemistry, vol. 5, No. 1, 1997, pp. 49–64.
Thomas D. Penning et al.: "Synthesis and Biological Evaluation of the 1,5–Diarylpyrazole Class of cyclooxygenase–2 Inhibitors: Identification of 4–[5–(4–Methylphenyl)–3–(trifluoromethyl)–1H–pyrazol–1–yl] benzenesulfonamide (SC–58635) Celecoxib)" Journal of Medicinal Chemistry, vol. 40, No. 9, 1997, pp. 1347–1365.
Gunnar J. Hanson.: "Pulmonary–Allergy, Dermatological, Gastrointestinal & Arthritis, Inhibitors of p38 kinase" Expert Opinion on Therapeutic Patients, vol. 7, No. 7, 1997, pp. 729–733.

* cited by examiner

Primary Examiner—Alan L. Rotman
Assistant Examiner—Rita Desai
(74) Attorney, Agent, or Firm—Wenderoth, Lind & Ponack L.L.P.

(57) ABSTRACT

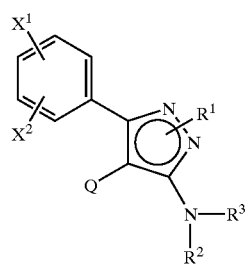

Aminopyrazole derivatives represented by formula (I), or salts thereof, wherein $X^1$ and $X^2$ are each a hydrogen atom or a halogen atom, or $X^1$ and $X^2$ may be united together to form a lower alkylenedioxy group, Q is a pyridyl group or a quinolyl group, $R^1$ is a hydrogen atom, a substituted or unsubstituted lower alkyl or aryl group, $R^2$ is a hydrogen atom, a lower alkyl group, or an aralkyl group, and $R^3$ represents a hydrogen atom, an organic sulfonyl group, or —C(=Y)—$R^4$ in which $R^4$ is a hydrogen atom or an organic residue and Y is an oxygen or sulfur atom, provided that, when $R^3$ is a hydrogen atom, $R^1$ is a group other than a hydrogen atom and $R^2$ is a hydrogen atom. These amimopyrazole derivatives or their salts have excellent p38MAP kinase inhibiting activities and are hence useful in the prevention or treatment of diseases associated with tumor necrosis sis factor α, interleukin 1, interleukin 6 or cyclooxygenase II.

23 Claims, No Drawings

AMINOPYRAZOLE DERIVATIVES

This application is a 371 of PCT/JP99/07186 filed Dec. 21, 1999.

TECHNICAL FIELD

This invention relates to novel aminopyrazole derivatives or salts thereof. More particularly, it relates to aminopyrazole derivatives represented by the following formula, or salts thereof.

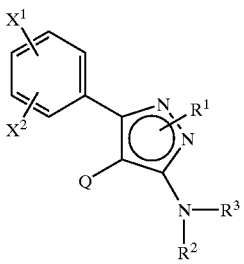

wherein:
- $X^1$ and $X^2$ each independently represent a hydrogen atom or a halogen atom, or when $X^1$ and $X^2$ are attached to positions adjacent to each other, they may be united together to form a lower alkylenedioxy group;
- Q represents a pyridyl group or a quinolyl group;
- $R^1$ represents a hydrogen atom, a substituted or unsubstituted lower alkyl group, or a substituted or unsubstituted aryl group;
- $R^2$ represents a hydrogen atom, a lower alkyl group, or an aralkyl group in which the aryl moiety may optionally be substituted;
- $R^3$ represents a hydrogen atom, an organic sulfonyl group, or —C(=Y)—$R^4$ in which $R^4$ is a hydrogen atom or an organic residue and Y is an oxygen or sulfur atom;
- provided that, when $R^3$ is a hydrogen atom, $R^1$ is a group other than a hydrogen atom and $R^2$ is a hydrogen atom.

BACKGROUND ART

TNF-α, IL-1, IL-6 and COX-II are proteins which are predominantly produced by immunocompetent cells such as macrophages and neutrophilic leukocytes, and constitute important factors participating, for example, in immunoregulatory functions and inflammatory symptoms. TNF-α and the like are also known as factors participating in many biological reactions in the hematopoietic system, the endocrine system, the nervous system and the like. Accordingly, the excessive or uncontrolled production of TNF-α and the like in the living body are believed to be closely related to the onset and aggravation of diseases associated with TNF-α and the like.

On the other hand, p38MAP kinase found within various types of cells in the living body are known to activate, in particular, some types of transcription factors. Specifically, transcription factors such as NF-κB, AP-1 and CREB bind to a certain DNA sequence common to TNF-α, IL-1, IL-6, COX-II and the like, and thereby promote transcription. Within the cell nucleus, these transcription factors are activated by the action of p38MAP kinase, so that proteins such as TNF-α are synthesized from the transcribed mRNA The mRNA which has gone out of the nucleus in the presence of calcium is inactivated by binding to a protein having a specific sequence, and decomposed rapidly. However, in the presence of p38MAP kinase activated by phosphorylation, the mRNA is released from the protein and thereby activated. Consequently, it is believed that the synthesis of proteins such as TNF-α, IL-1, IL-6 and COX-II is also promoted along this pathway.

Accordingly, it is believed that the production of TNF-α, IL-1, IL-6, COX-II and the like can be hindered by inhibiting p38MAP kinase. On the basis of this concept, there have been proposed a number of compounds which have a p38MAP kinase inhibiting activity and thereby hinder the production of TNF-α, IL-1, IL-6, COX-II and the like (see, for example, Bioorganic & Medicinal Chemistry, Vol. 5, No. 1, pp. 49–64, 1997; and Japanese Patent Laid-Open No. 503017/'95).

It is expected that these TNF-α, IL-1, IL-6 or COX-II production inhibitors will be effective in the treatment or prevention of diseases associated with TNF-α, IL-1, IL-6 or COX-II, such as rheumatoid arthritis, multiple sclerosis, osteoarthritis, psoriasis, viral and bacterial infections, asthma, septic shock, IBD, Crohn's disease, Alzheimer's disease, diabetes, cachexia, osteoporosis, graft versus host disease, adult RDS, arteriosclerosis, gout, glomerulonephritis, congestive heart failure, ulcerative colitis, sepsis, cerebral malaria, restenosis, hepatitis, SLE, thrombosis, born resorption disease, chronic pulmonary inflammation disease, cardiac reperfusion injury, renal reperfusion injury, cancer, Reiter's syndrome, preterm labor, eczema, allograft rejection, stroke, fever, Behçet's disease, neuralgia, meningitis, sunburn, contact dermatitis, acute synovitis, spondylitis, muscle degeneration, angiogenesis, conjunctivitis, psoriatic arthritis, viral myocarditis, pancreatitis, glioblastoma, bleeding, joint inflammation, endotoxic shock, parasitic infections, tuberculosis, myocardial infarction, leprosy, diabetic retinopathy, IBS, transplant rejection, burns, bronchitis, ischemic heart disease, eclampsia, pneumonia, remission of swelling, low back pain, laryngopharyngitis, Kawasaki disease, myelopathy and atopic dermatitis.

Meanwhile, as to aminopyrazole derivatives, there have been known some aminopyrazole derivatives in which the 3- or 5-position of the pyrazole ring is substituted by a pyridyl group or an optionally substituted amino group, the 5- or 3-position is substituted by a pyridyl group, and the 4-position is substituted by a pyridyl group or an optionally substituted phenyl group (Japanese Patent Laid-Open No. 17470/'93). However, neither description nor suggestion is found therein about their p38MAP kinase inhibiting activities.

Very recently, certain aminopyrazole derivatives having p38MAP kinase inhibiting activities have been proposed (see the pamphlets of PCT International Publications WO98/52940 and WO98/52941).

The present inventors have now found that aminopyrazole derivatives in which one of the 3- and 5-positions of the pyrazole ring is substituted by an optionally substituted amino group, the other of the 3- and 5-positions thereof is substituted by a phenyl group that may be substituted by a halogen atom or a lower alkylenedioxy group, and the 4-position thereof is substituted by a pyridyl or quinolyl group have excellent p38MAP kinase inhibiting activities and are hence effective in hindering the production of TNF-α, IL-1, IL-6, COX-II and the like.

Thus, the present invention provides aminopyrazole derivatives represented by the above formula (I), or salts thereof

DISCLOSURE OF THE INVENTION

The term "lower" as used herein means that the group or compound modified by this term has 6 or less carbon atoms and preferably 4 or less carbon atoms.

Thus, examples of the "lower alkyl group" include methyl, ethyl, n-propyl isopropyl, n-butyl, isobutyl sec-butyl, t-butyl, n-pentyl and n-hexyl, and examples of the "lower alkylenedioxy group" include methylenedioxy, ethylenedioxy and propylenedioxy.

The "aryl group" or the aryl moiety of the "aralkyl group" may be a monocyclic or polycyclic aromatic ring, and examples thereof include phenyl and naphthyl.

The "organic sulfonyl group" is a residue obtained by eliminating a hydroxyl group from an organic sulfonic acid, and examples thereof include methanesulfonyl ethanesulfonyl, benzenesulfonyl and p-toluenesulfonyl. On the other hand, the term "halogen atom" comprehends fluorine, chlorine, bromine and iodine atoms.

The "pyridyl group or quinolyl group" represented by the symbol Q may preferably be a 4-pyridyl group or a 4-quinolyl group.

The substituents which can be present in the "substituted or unsubstituted lower alkyl group" represented by the symbol $R^1$ include, for example, halogen, hydroxyl, lower alkoxy, lower alkanoyloxy, aralkyloxy, amino, lower alkylamino, di(lower alkyl)amino, aralkyloxycarbonylamino and lower alkoxycarbonylamino. The lower alkyl group may be substituted by one or two substituents selected from the foregoing. The substituents which can be present in the "substituted or unsubstituted aryl group" represented by the symbol $R^1$ include, for example, halogen, lower alkyl, halogeno(lower alkyl), lower alkoxy, lower alkylenedioxy, hydroxyl, aralkyloxy, lower alkanoyloxy, mercapto, lower alkylthio, amino, lower alkoxycarbonylamino and nitro. The aryl group may be substituted by one or two substituents selected from the foregoing.

The substituents which can be present in the aryl moiety of the "aralkyl group in which the aryl moiety may optionally be substituted" represented by the symbol $R^2$ may be the same as described above for the substituent(s) present in the aryl group represented by the symbol $R^1$.

The "organic residue" represented by the symbol $R^4$ may be any residue derived from an organic compound without any particular limitation. As used herein, however, the term "organic residue" generally comprehends substituted or unsubstituted, saturated or unsaturated straight-chain, branched or cyclic hydrocarbon radicals, substituted or unsubstituted heterocyclic groups, substituted or unsubstituted amino groups, and substituted carbonyl groups.

The "substituted or unsubstituted, saturated or unsaturated straight-chain, branched or cyclic hydrocarbon radicals" preferably include substituted or unsubstituted alkyl groups, substituted or unsubstituted alkenyl groups, substituted or unsubstituted alkynyl groups, substituted or unsubstituted cycloalkyl groups, substituted or unsubstituted cycloalkenyl groups, substituted or unsubstituted aryl groups, substituted or unsubstituted bridged cycloalkyl groups, and substituted or unsubstituted spiroalkyl groups. More preferably, they include substituted or unsubstituted alkyl groups, substituted or unsubstituted cycloalkyl groups, and substituted or unsubstituted aryl groups. Among them, substituted or unsubstituted lower alkyl groups are especially preferred.

As used herein, the term "alkyl group" generally comprehends straight-chain or branched alkyl groups having 1 to 20 carbon atoms. Examples thereof include, in addition to the above-described lower alkyl groups, 5-methylhexyl, n-octyl, n-decyl, n-dodecyl, n-hexadecyl and n-octadecyl. The term "alkenyl group" generally comprehends straight-chain or branched alkenyl groups having 2 to 20 carbon atoms, and examples thereof include vinyl, allyl, 1-propenyl, isopropenyl, 2-butenyl, 1,3-butadienyl, 2-pentenyl, 1,4-hexadienyl and 9-octadecenyl. The term "alkynyl group" generally comprehends straight-chain or branched alkynyl groups having 2 to 20 carbon atoms, and examples thereof include ethynyl, 2-propynyl and 4-pentynyl. The term "cycloalkyl group" generally comprehends cycloalkyl groups having 3 to 10 carbon atoms, and examples thereof include cyclopropyl, cyclobutyl, cyclopentyl, cyclohexyl, cycloheptyl and cyclooctyl. The term "cycloalkenyl group" generally comprehends cycloalkenyl groups having 4 to 10 carbon atoms, and examples thereof include 2-cyclobutenyl, 2-cyclopentenyl and 2-cyclohexenyl. The term "aryl group" generally comprehends monocyclic or polycyclic aryl groups having 6 to 20 carbon atoms, and examples thereof include phenyl, 1-indenyl, 1-naphthyl, 2-naphthyl, 1-azulenyl, 2-anthryl, 2-phenanthryl and 1-acenaphthenyl. Moreover, the term "bridged cycloalkyl group" generally comprehends bridged cycloalkyl groups having 4 to 20 carbon atoms, and examples thereof include bicyclo[2.2.1]hept-2-yl, bicyclo[3.2.1]oct-2-yl, bicyclo[4.3.2]undec-2-yl and adamantyl. The term "spiroalkyl group" generally comprehends spiroalkyl groups having 7 to 20 carbon atoms, and examples thereof include spiro[4.5]dec-2-yl and spiro[5.5]dec-3-yl.

The heterocyclic group present in the "substituted or unsubstituted heterocyclic group" used herein may preferably be a monocyclic or polycyclic, saturated or partially saturated, or aromatic heterocycle which contains 1 to 4 heteroatoms selected from N, O and S and has a four- to eight-membered ring. Alternatively, the heterocycle may further be fused with a cyclic hydrocarbon to form a fused ring. Among such heterocyclic groups, more preferred ones are monocyclic or bicyclic, saturated or aromatic heterocyclic groups which contain 1 or 2 heteroatoms selected from N, O and S and have a five- or six-membered ring, and which may optionally be fused with a phenyl group.

Thus, these "heterocyclic groups" include, for example, monocyclic heteroaryl groups such as pyrrolyl, furyl, thienyl imidazolyl, pyrazolyl, oxazolyl isoxazolyl thiazolyl triazolyl, thiadiazolyl, tetrazolyl pyridyl, pyranyl pyrimidinyl pyridazinyl, pyrazinyl azepinyl and azocinyl polycyclic heteroaryl groups such as purinyl naphthidinyl and pteridinyl; heteroaryl groups fused with a cyclic hydrocarbon radical to form a fused ring, such as benzothienyl benzofuranyl indolyl isoindolyl, indazolyl, benzimidazolyl, benzoxazolyl, benzothiazolyl quinolyl isoquinolyl, chromenyl phthalazinyl quinazolinyl quinoxalinyl carbazolyl phenanthridinyl, acridinyl and dibenzazepinyl; saturated heterocyclic groups such as azetidinyl pyrrolidinyl, tetrahydrofuranyl piperidinyl, piperazinyl and morpholinyl; and partially saturated heterocyclic groups fused with a cyclic hydrocarbon radical to form a fused ring, such as indolinyl isoindolinyl 1,2,3,4-tetrahydroisoquinolyl chromanyl and isochromanyl.

Moreover, the "substituted or unsubstituted amino groups" used in the definition of the aforesaid "organic residue" include, for example, lower alkylamino groups, di(lower alkyl)amino groups, and substituted or unsubstituted arylamino groups, in addition to the unsubstituted amino group. Among them, substituted or unsubstituted arylamino groups are preferred.

The term "substituted carbonyl groups" used in the definition of the aforesaid "organic residue" means carbonyl groups substituted by an organic group. Preferred examples thereof include substituted or unsubstituted alkyloxycarbonyl groups, substituted or unsubstituted alkylcarbonyl groups, and substituted or unsubstituted arylcarbonyl groups. Among them, substituted or unsubstituted lower alkyloxycarbonyl groups and substituted or unsubstituted phenylcarbonyl groups are more preferred.

The substituents which can be present in the "substituted or unsubstituted alkyl groups" used in the definition of the organic residue include, for example, halogen, hydroxyl lower alkoxy, lower alkanoyloxy, arylcarbonyloxy, aryloxy, mercapto, lower alkylthio, lower alkanoylthio, arylcarbonylthio, arylthio, amino, lower alkylamino, di(lower alkyl)amino, lower alkanoylamino, arylcarbonylamino, aralkyloxycarbonylamino, lower alkoxycarbonylamino, N-(lower alkyl)-N-(lower alkoxycarbonyl)amino, guanidino, carboxyl, lower alkoxycarbonyl, aralkyloxycarbonyl, carbamoyl, lower alkylcarbonyl, arylcarbonyl, cycloalkyl aryl [this aryl may optionally be substituted by 1 to 5 substituents selected from halogen, lower alkyl, halogeno(lower alkyl), lower alkoxy, lower alkylenedioxy, hydroxyl, aralkyloxy, lower alkanoyloxy, mercapto, lower alkylthio, amino, lower alkylamino, di(lower alkyl)amino, lower alkanoylamino, aralkyloxycarbonylamino, lower alkoxycarbonylamino and nitro], and monocyclic or bicyclic heterocyclic groups which contain 1 or 2 heteroatoms selected from N, S and O and have a five- or six-membered ring and which may further be fused with a benzene ring (these heterocyclic groups may optionally be substituted by 1 or 2 substituents selected from halogen, lower alkyl, lower alkoxy and nitro). The alkyl group may be substituted by 1 to 3 substituents selected from the foregoing ones. Among others, preferred ones are lower alkyl groups which may be substituted by 1 or 2 substituents selected from halogen, hydroxyl, lower alkoxy, lower alkanoyloxy, aryloxy, amino, lower alkylamino, di(lower alkyl)amino, aralkyloxycarbonylamino, lower alkoxycarbonylamino, N-(lower alkyl)-N-(lower alkoxycarbonyl)amino, carboxyl, lower alkoxycarbonyl, lower cycloalkyl, aryl [this aryl may optionally be substituted by 1 to 5 halogen atoms, or 1 to 3 substituents selected from lower alkyl, halogeno(lower alkyl), lower alkoxy, lower alkylenedioxy, hydroxyl, aralkyloxy, lower alkanoyloxy, mercapto, lower alkylthio, amino, lower alkoxycarbonylamino and nitro], and monocyclic or bicyclic heteroaryl groups which contain 1 or 2 heteroatoms selected from N and S and have a five- or six-membered ring and which may further be fused with a benzene ring (these heteroaryl groups may optionally be substituted by a lower alkyl group or groups). Among them, especially preferred ones are lower alkyl groups substituted by an aryl group [this aryl group may optionally be substituted by 1 to 5 halogen atoms, or 1 to 3 substituents selected from lower alkyl, halogeno(lower alkyl), lower alkoxy, lower alkylenedioxy, hydroxyl, aralkyloxy, lower alkylthio, amino and nitro], or a five- or six-membered heteroaryl group containing 1 or 2 heteroatoms selected from N and S (this heteroaryl group may optionally be substituted by one lower alkyl group).

The substituents which can be present in the "substituted or unsubstituted alkenyl groups" used in the definition of the organic residue include, for example, halogen and aryl [this aryl may optionally be substituted by 1 to 5 substituents selected from halogen, lower alkyl, halogeno(lower alkyl), lower alkoxy, lower alkylenedioxy, hydroxyl, aralkyloxy, lower alkanoyloxy, mercapto, lower alkylthio, amino, lower alkylamino, di(lower alkyl)amino, lower alkanoylamino, aralkyloxycarbonylamino, lower alkoxycarbonylamino and nitro]. The alkenyl group may be substituted by 1 or 2 substituents selected from the foregoing ones. Among them, unsubstituted alkenyl groups having 2 to 4 carbon atoms are especially preferred.

The substituents which can be present in the "substituted or unsubstituted cycloalkyl groups" used in the definition of the organic residue include, for example, lower alkyl, hydroxyl, lower alkoxy, lower alkanoyloxy, carboxyl, lower alkoxycarbonyl and oxo. The cycloalkyl group may be substituted by 1 or 2 substituents selected from the foregoing ones. Among them, unsubstituted cycloalkyl groups having 5 to 7 carbon atoms are especially preferred.

The substituents which can be present in the "substituted or unsubstituted aryl groups" used in the definition of the organic residue include, for example, halogen, lower alkyl, lower alkoxy, lower alkylenedioxy, hydroxyl, aralkyloxy, lower alkanoyloxy, mercapto, lower alkylthio, amino, lower alkylamino, di(lower alkyl)amino, lower alkanoylamino and nitro. The aryl group may be substituted by 1 to 3 substituents selected from the foregoing ones. Among them, unsubstituted aryl groups having 6 to 10 carbon atoms are especially preferred.

The substituents which can be present in the "substituted or unsubstituted heterocyclic groups" used in the definition of the organic residue include, for example, halogen, lower alkyl lower alkoxy, lower alkylenedioxy, hydroxyl, lower alkanoyloxy, amino, lower alkylamino, di(lower alkyl) amino, lower alkanoylamino, aralkyloxycarbonyl, lower alkoxycarbonyl and nitro. The heterocyclic group may be substituted by 1 to 3 substituents selected from the foregoing ones. Among them, especially preferred ones are monocyclic or bicyclic heterocyclic groups which contain 1 or 2 heteroatoms selected from N and O and have a five- or six-membered ring, which may optionally be substituted by one aralkyloxycarbonyl group or lower alkoxycarbonyl group, and which may further be fused with a benzene ring.

The "substituted or unsubstituted arylamino groups" used in the definition of the substituted or unsubstituted amino groups include, for example, arylamino groups in which the aryl moiety may optionally be substituted by 1 to 5 halogen atoms, or 1 to 3 substituents selected from lower alkyl, halogeno(lower alkyl), lower alkoxy, lower alkylenedioxy, hydroxyl, aralkyloxy, lower alkanoyloxy, lower alkylthio, amino and nitro.

Furthermore, the "substituted or unsubstituted lower alkyloxycarbonyl groups" used in the definition of the substituted carbonyl groups include, for example, lower alkyloxycarbonyl groups which may optionally be substituted by 1 or 2 substituents selected from hydroxyl, lower alkoxy, amino, lower alkylamino and aryl [this aryl may optionally be substituted by 1 to 5 substituents selected from halogen, lower alkyl halogeno(lower alkyl), lower alkoxy, lower alkylenedioxy, hydroxyl, aralkyloxy, lower alkanoyloxy, mercapto, lower alkylthio, amino, lower alkoxycarbonylamino and nitro]. Among them, unsubstituted lower alkyloxycarbonyl groups are especially preferred.

The "substituted or unsubstituted phenylcarbonyl groups" used in the definition of the substituted carbonyl groups include, for example, phenylcarbonyl groups which may optionally be substituted by 1 to 3 substituents selected from halogen, lower alkyl, lower alkoxy, hydroxyl amino, lower alkoxycarbonylamino and nitro. Among them, unsubstituted phenylcarbonyl groups are especially preferred.

Furthermore, the "aralkyl group" as used herein is an alkyl group substituted by an aryl group. Preferred examples thereof include aryl-substituted lower alkyl groups such as benzyl, 1-phenyl-ethyl 2-phenylethyl, 1-phenylpropyl, 3-phenylpropyl, 4-phenylbutyl, 1-naphthylmethyl, 2-naphthylmethyl and diphenylmethyl.

The "lower alkoxy group" is a lower alkyloxy group in which the lower alkyl moiety has the above-defined meaning. Examples thereof include methoxy, ethoxy, n-propoxy, i-propoxy, n-butoxy and t-butoxy.

The "lower alkanoyloxy group" is a lower alkylcarbonyloxy group in which the lower alkyl moiety has the above-defined meaning. Examples thereof include acetoxy, propionyloxy, butyryloxy and valeryloxy.

Examples of the "arylcarbonyloxy group" include benzoyloxy, 4-nitrobenzoyloxy and 2-naphthoyloxy.

Examples of the "aryloxy group" include phenoxy, 4-methylphenoxy and 2-naphthoxy.

Examples of the "aralkyloxy group" include benzyloxy, 1-phenylethyloxy, 2-phenylethyloxy, 1-phenylpropyloxy and 3-phenylpropyloxy.

Examples of the "lower alkylthio group" include methylthio, ethylthio and isopropylthio.

Examples of the "lower alkanoylthio group" include acetylthio and propionylthio.

Examples of the "arylcarbonylthio group" include benzoylthio and 1-naphthoylthio.

Examples of the "arylthio group" include phenylthio and 2-naphthylthio.

Examples of the "lower alkylamino group" include methylamino, ethylamino and n-propylamino.

Examples of the "di(lower alkyl)amino group" include dimethylamino, diethylamino and di-n-propylamino.

Examples of the "lower alkanoylamino group" include acetylamino and propionylamino.

Examples of the "arylcarbonylamino group" include benzoylamino.

Examples of the "aralkyloxycarbonylamino group" include benzyloxycarbonylamino, 4-bromobenzyloxycarbonylamino, 4-methoxybenzyloxycarbonylamino and 4-nitrobenzyloxycarbonylamino.

Examples of the "lower alkoxycarbonylamino group" include t-butoxycarbonylamino.

Examples of the "N-(lower alkyl)-N-(lower alkoxy)-carbonylamino group" include N-methyl-N-t-butoxycarbonylamino and N-ethyl-N-t-butoxycarbonylamino.

Examples of the "lower alkoxycarbonyl group" include methoxycarbonyl ethoxycarbonyl and t-butoxycarbonyl.

Examples of the "aralkyloxycarbonyl group" include benzyloxycarbonyl, 4-methoxybenzyloxycarbonyl and 4-nitrobenzyloxycarbonyl.

Examples of the "lower alkylcarbonyl group" include acetyl and propionyl.

Examples of the "arylcarbonyl group" include benzoyl.

Examples of the "halogenated lower alkyl group" include trifluoromethyl 2,2,2-trifluoroethyl and pentafluoroethyl.

One preferred class of compounds in accordance with the present invention are the compounds of formula (I) in which $X^1$ is 4-fluoro and $X^2$ is hydrogen.

Another preferred class of compounds in accordance with the present invention are the compounds of formula (I) in which Q is 4-pyridyl.

Still another preferred class of compounds in accordance with the present invention are the compounds of formula () in which $R^1$ is unsubstituted lower alkyl.

A further preferred class of compounds in accordance with the present invention are the compounds of formula (I) in which $R^2$ is hydrogen or methyl.

A still further preferred class of compounds in accordance with the present invention are the compounds of formula (I) in which $R^3$ is —C(=Y)—$R^4$ and Y is oxygen.

Where $R^1$ represents a hydrogen atom in the compounds of the above formula (I) in accordance with the present invention, such hydrogen atoms are usually attached to one of the two nitrogen atoms constituting the pyrazole ring, at a certain ratio depending on the reaction conditions and the like. Consequently, the position at which $R^1$ is substituted cannot be specified. Accordingly, the representation of the position of the substituent $R^1$ as used in the chemical structural formula given herein means that, "where $R^1$ represents a hydrogen atom, it is unknown which of the two nitrogen atoms constituting the pyrazole ring $R^1$ is attached to." Where $R^1$ represents a group other than a hydrogen atom, the position at which $R^1$ is substituted can be specified. Accordingly, the above-described representation means that "where $R^1$ represents a group other than a hydrogen atom, $R^1$ is attached to a fixed one of the two nitrogen atoms constituting the pyrazole ring."

In the notation of compounds in the examples and elsewhere, they are represented in such a way that, when $R^1$ is a hydrogen atom, the amino group which may be substituted is attached to the 3-position of the pyrazole ring.

In addition to the compounds described in the examples which will be given later, typical examples of the compounds of the above formula (I) which are provided by the present invention include:

5-(4-fluorophenyl)-3-methanesulfonylamino-4-(4-pyridyl) pyrazole, 5-(3-chloro-4-fluorophenyl)-3-(4-methylbenzenesulfonylamino)-4-(4-pyridyl)pyrazole, 3-acetylamino-5-(4-fluorophenyl)-4-(4-pyridyl)pyrazole, 3-(4-fluorophenyl)-5-isobutyrylamino-1-methyl-4-(4-pyridyl)pyrazole, 3-(4-fluorophenyl)-5-methyl-4-(4-pyridyl)-5-(3-trifluoroacetylamino)pyrazole, 3-(3-chloropropionylamino)-5-(4-fluorophenyl)-4-(4-pyridyl)pyrazole, 3-(4-fluorophenyl)-5-hydroxyacetylamino-1-methyl-4-(4-pyridyl)pyrazole, 5-(4-fluorophenyl)-3-(3-hydroxypropionylamino)-4-(4-pyridyl)pyrazole, 3-(4-fluorophenyl)-5-methoxyacetylamino-1-methyl-4-(4-pyridyl)pyrazole, 3-ethoxyacetylamino-5-(4-fluorophenyl)-4-(4-pyridyl) pyrazole, 3-acetoxyacetylamino-5-(4-fluorophenyl)-4-(4-pyridyl) pyrazole, 3-benzoyloxyacetylamino-5-(4-fluorophenyl)-4-(4-pyridyl) pyrazole, 3-(4-fluorophenyl)-1-methyl-5-phenoxyacetylamino-4-(4-pyridyl)pyrazole, 5-(4-fluorophenyl)-3-mercaptoacetylamino-4-(4-pyridyl) pyrazole, 3-(4-fluorophenyl)-1-methyl-5-methylthioacetylamino-4-(4-pyridyl)pyrazole, 3-acetylthioacetylamino-5-(4-fluorophenyl)-4-(4-pyridyl) pyrazole, 3-benzoylthioacetylamino-5-(4-fluorophenyl)-4-(4-pyridyl) pyrazole, 3-(4-fluorophenyl)-1-methyl-5-phenylthioacetylamino-4-(4-pyridyl)pyrazole, 5-aminoacetylamino-3-(4-fluorophenyl)-1-methyl-4-(4-pyridyl)pyrazole, 3-(3-aminopropionylamino)-5-(4-fluorophenyl)-4-(4-pyridyl)pyrazole,
5-(4-fluorophenyl)-3-(L-leucylamino)-4-(4-pyridyl)pyrazole,
5-(4-fluorophenyl)-3-methylamnioacetylamio-4-(4-pyridyl)pyrazole,
5-diethylaminoacetylamino-3-(4-fluorophenyl)-1-methyl-4-(4-pyridyl)pyrazole,
5-acetylaminoacetylamino-3-(4-fluorophenyl)-1-methyl-4-(4-pyridyl)pyrazole,
5-benzoylaminoacetylamino-3-(4-fluorophenyl)-1-methyl-4-(4-pyridyl)pyrazole,
3-(N'-p-methoxycarbobenzoxy-L-alanylamino)-5-(4-fluorophenyl)-4-(4-pyridyl)pyrazole,
3-(N'-carbo-t-butoxy-glycylamino)-5-(4-fluorophenyl)-4-(4-pyridyl)pyrazole,
3-L-arginylamino-5-(4-fluorophenyl)-4-(4-pyridyl)pyrazole,
5-(3-carboxypropionylamino)-3-(4-fluorophenyl)-1-methyl-4-(4-pyridyl)pyrazole,
3-(3-t-butoxycarbonylpropionylamino)-5-(4-fluorophenyl)-4-(4-pyridyl)pyrazole,
3-(3-benzyloxycarbonylpropionylamino)-5-(4-fluorophenyl)-4-(4-pyridyl)pyrazole,
3-(3-carbamoylpropionylamino)-5-(4-fluorophenyl)-4-(4-pyridyl)pyrazole,
3-(3-acetylpropionylamino)-5-(4-fluorophenyl)-4-(4-pyridyl)pyrazole,
3-(3-benzoylpropionylamino)-5-(4-fluorophenyl)-4-(4-pyridyl)pyrazole,
3-cyclopentylacetylamino-5-(4-fluorophenyl)-4-(4-pyridyl)pyrazole,
5-cyclohexylacetylamino-3-(4-fluorophenyl)-1-methyl-4-(4-pyridyl)pyrazole,
5-(4-fluorophenyl)-3-(4-phenylbutyrylamino)-4-(4-pyridyl)pyrazole,
5-(4-fluorophenyl)-3-(2-fluorophenylacetylamino)-4-(4-pyridyl)pyrazole,
3-(4-acetoxyphenylacetylamino)-5-(4-fluorophenyl)-4-(4-pyridyl)pyrazole,
5-(4-fluorophenyl-3-(2-methoxyphenylacetylamino)-4-(4-pyridyl)pyrazole,
5-(4-fluorophenyl)-3-(2,3-dimethoxyphenylacetylamino)-4-(4pyridyl)pyrazole,
5-(4-fluorophenyl)-3-(2,3-methylenedioxyphenylacetylamino)-4-(4-pyridyl)pyrazole,
5-(4-fluorophenyl)-3-(4-hydroxyphenylacetylamino)-4-(4-pyridyl)pyrazole,
3-(4-aminophenylacetylamino)-5-(4-fluorophenyl)-4-(4-pyridyl)pyrazole,
5-(4-fluorophenyl)-3-(4-dimethylamminophenylacetylamino)-4-(4-pyridyl)pyrazole,
3-(4-acetylaminophenylacetylamino)-5-(4-fluorophenyl)-4-(4-pyridyl)pyrazole,
5-(2-bromo-4-fluorophenylacetylamino)-3-(4-fluorophenyl)-1-methyl-4-(4-pyridyl)pyrazole,
5-(4-chloro-2-fluorophenylacetylamino)-3-(4-fluorophenyl)-1-methyl-4-(4-pyridyl)pyrazole,
5-(2-chloro-4-methylphenylacetylamino)-3-(4-fluorophenyl)-1-methyl-4-(4-pyridyl)pyrazole,
5-(2-chloro-4-methoxyphenylacetylamino)-3-(4-fluorophenyl)-1-methyl-4-(4-pyridyl)pyrazole,
5-(2-chloro-4-trifluromethylphenylacetylamino)-3-(4-fluorophenyl)-1-methyl-4-(4-pyridyl)pyrazole,
5-(2-chloro-4-hydroxyphenylacetylamino)-3-(4-fluorophenyl)-1-methyl-4-(4-pyridyl)pyrazole,
5-(4-amino-2-chlorophenylacetylamino)-3-(4-fluorophenyl)-1-methyl-4-(4-pyridyl)pyrazole,
5-(2-chloro-4-nitrophenylacetylamino)-3-(4-fluorophenyl)-1-methyl-4-(4-pyridyl)pyrazole,
5-(2-ethylphenylacetylamino)-3-(4-fluorophenyl)-1-methyl-4-(4-pyridyl)pyrazole,
5-(2,4-ditrifluromethylphenylacetylamino)-3-(4-fluorophenyl)-1-methyl-4-(4-pyridyl)pyrazole,
3-(4-fluorophenyl)-5-(2-hydroxyphenylacetylamino)-1-methyl-4-(4-pyridyl)pyrazole,
5-(4-acetoxyphenylacetylamino)-3-(4-fluorophenyl)-1-methyl-4-(4-pyridyl)pyrazole,
3-(4-fluorophenyl)-5-(4-mercaptophenylacetylamino)-1-methyl-4-(4-pyridyl)pyrazole,
3-(4-fluorophenyl)-1-methyl-5-(2-methylthiophenylacetylamino)-4-(4-pyridyl)pyrazole,
5-(4-dimethylaminophenylacetylamino)-3-(4-fluorophenyl)-1-methyl-4-(4-pyridyl)pyrazole,
5-(2-acetylaminophenylacetylamino)-3-(4-fluorophenyl)-1-methyl-4-(4-pyridyl)pyrazole,
5-(4-fluorophenyl)-4-(4-pyridyl)-3-(L-tyrosylamino)pyrazole,
5-(4-fluorophenyl)-4-(4-pyridyl)-3-(2-pyridylacetylamino)pyrazole,
5-(4-fluorophenyl)-4-(4-pyridyl)-3-(2-quinolylacetylamino)pyrazole,
5-(4-fluorophenyl)-3-(3-piperidinopropionylamino)-4-(4-pyridyl)pyrazole,
5-(4-fluorophenyl)-4-(4-pyridyl)-3-(L-tryptophylamino)pyrazole,
3-cyclohexylcarbonylamino-5-(4-fluorophenyl)-4-(4-pyridyl)pyrazole,
5-(4-fluorophenyl)-3-(4-hydroxycyclohexylcarbonylamino)-4-(4-pyridyl)pyrazole,
5-(4-fluorophenyl)-4-(4-pyridyl)-3-(4-pyridylcarbonylamino)pyrazole,
5-(4-fluorophenyl)-3-(3-furoylamino)-4-(4-pyridyl)pyrazole,
5-(4-fluorophenyl)-4-(4-pyridyl)-3-(2-thenoylamino)pyrazole,
5-(4-fluorophenyl)-4-(4-pyridyl)-3-(2-quinolylcarbonylamino)pyrazole,
5-(4-fluorophenyl)-3-(4-methylpiperazinylcarbonylamino)-4-(4-pyridyl)pyrazole,
5-(3-chloro-4-fluorophenyl)-3-phenylacetylamino-4-(4-pyridyl)pyrazole,
3-(3-chloro-4-fluorophenyl)-5-(2-chlorophenylacetylamino)-1-methyl-4-(4-pyridyl)pyrazole,
5-(3-chloro-4-fluorophenyl)-3-(2-phenylpropionylamino)-4-(4-pyridyl)pyrazole,
3-methoxalylamino-5-(4-fluorophenyl)-4-(4-pyridyl)pyrazole,
5-(4-fluorophenyl)-3-phenyloxalylamino-4-(4-pyridyl)pyrazole,
3-(4-fluorophenyl)-1-methyl-5-[phenyl(thioacetyl)amino]-4-(4-pyridyl)pyrazole,
5-(4-fluorophenyl)-3-(2-phenylpropionylamino)-4-(4-quinolyl)pyrazole,
3-(4-chlorophenylacetylamino)-5-(4-fluorophenyl)-4-(4-quinolyl)pyrazole,
3-(4-fluorophenyl)-5-[N-(2-fluorophenylacetyl)-N-methylamino]-1-methyl-4-(4-pyridyl)pyrazole,
5-[N-(2-bromophenylacetyl)-N-methylamino]-3-(4-fluorophenyl)-1-methyl-4-(4-pyridyl)pyrazole,
5-[N-(2-chloro-4-fluorophenylacetyl)-N-methylamino]-3-(4-fluorophenyl)-1-methyl-4-(4-pyridyl)pyrazole, 5-[N-(2,5-difluorophenylacetyl)-N-methylamino]-3-(4-fluorophenyl)-1-methyl-4-(4-pyridyl)pyrazole, 5-(N-ethyl-N-phenylacetylamino)-3-(4-fluorophenyl)-1-methyl-4-(4-pyridyl)pyrazole, 1-ethyl-5-(N-ethyl-N-phenylacetylamino)-3-(4-fluorophenyl)-4-(4-pyridyl)pyrazole, 1-(2-hydroxyethyl)-5-[N-(2-hydroxyethyl)-N-phenylacetylamino]-3-(4-fluorophenyl)-4-(4-pyridyl)pyrazole, 5-(N-benzyl-N-phenylacetylamino)-3-(4-fluorophenyl)-1-methyl-4-(4-pyridyl)pyrazole, 5-[N-(4-chlorophenylmethyl)-N-phenylacetylamino]-3-(4-fluorophenyl)-1-methyl-4-(4-pyridyl)pyrazole, and the like.

The compounds of formula (I) in accordance with the present invention can form salts. Examples of such salts include salts formed with inorganic acids such as hydrochloric acid, hydrobromic acid, sulfuric acid, nitric acid and phosphoric acid; and salts formed with organic acids such as acetic acid, oxalic acid, citric acid, lactic acid, tartaric acid and p-toluenesulfonic acid. Among others, pharmaceutically acceptable salts are preferred.

According to the present invention, depending on the types of the substituents represented by $R^1$, $R^2$ and $R^3$, the compounds of the above formula (1) may be prepared, for example, by any of the processes (a) to (e) described below.

Process (a): The compounds of the above formula (I) in which $R^2$ is a hydrogen atom, $R^3$ is —C(=Y)—$R^4$, and Y is an oxygen atom may be prepared by:

(i) reacting an amino compound of the formula

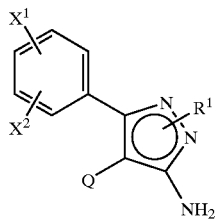

(II)

wherein $X^1$, $X^2$, Q and $R^1$ have the above-defined meanings, with a carboxylic acid of the formula $R^4$—COOH (II)

wherein $R^4$ has the above-defined meaning, or a reactive derivative thereof; or (ii) reacting a reactive derivative of an amino compound of the above formula (II) with a carboxylic acid of the above formula (III).

Process (b): The compounds of the above formula (I) in which $R^3$ is —C(=Y)—$R^4$ and Y is a sulfur atom may be prepared by treating a compound of formula (I) in which Y is an oxygen atom, with the Lawesson reagent.

Process (c): The compounds of the above formula (I) in which $R^2$ is a hydrogen atom and $R^3$ is an organic sulfonyl group may be prepared by treating a compound of the above formula (II) with an organic sulfonic acid or a reactive derivative thereof.

Process (d): The compounds of the above formula (I) in which $R^1$ is a substituted or unsubstituted lower alkyl group may be prepared by alkylating a compound of formula (I) in which $R^1$ is a hydrogen atom, for example, by treating it with a substituted or unsubstituted lower alkyl halide.

Process (e): The compounds of the above formula (I) in which $R^2$ is a lower alkyl group or an aralkyl group having an optionally substituted aryl moiety may be prepared by alkylating or aralkylating a compound of formula (I) in which $R^2$ is a hydrogen atom, for example, by treating it with a lower alkyl halide or an aralkyl halide.

In the above-described process (a) (i), the reaction of the amino compound of formula (II) with the carboxylic acid of formula (III) or its reactive derivative (e.g., acid chloride, acid anhydride, mixed acid anhydride, activated amide or activated ester) may generally be carried out in an inert organic solvent selected, for example, from ethers such as dioxane, tetrahydrofuran and dimethoxyethane; aromatic hydrocarbons such as benzene, toluene and xylene; halogenated hydrocarbons such as dichloromethane and chloroform; amides such as dimethylformamide and dimethylacetamide; and dimethyl sulfoxide. If necessary, this reaction may also be carried out in the presence of a base such as 1,8-diazabicyclo[5.4.0]-undec-7-ene (DBU), triethylamine, diisopropylethylamine, dimethylaminopyridine, pyridine or N-methylmorpholine. The reaction temperature may vary according to the type of the carboxylic acid of formula (II) or its reactive derivative used. However, it is usually suitable to employ a temperature ranging from −10° C. to the reflux temperature of the reaction mixture and preferably from an ice-cold temperature to about 50° C.

In the above-described process (a) (i), when a free carboxylic acid is used as the carboxylic acid of formula (III), it is preferable to treat the carboxylic acid, for example, with 1,1-carbonyldiimizadole or 1,1-thionyldiimizadole in advance and thereby convert it to a reactive derivative (e.g., imidazolide).

When an acid chloride is used as the reactive derivative, it is possible to treat the acid chloride, for example, with imidazole or DBU in advance, and thereby convert it to another reactive derivative (e.g., imidazolide) prior to reaction.

When an acid chloride or a mixed acid anhydride is used as the reactive derivative, not only a carboxylic residue is introduced into the desired amino group at the 3-position of the pyrazole ring, but also another carboxylic residue may be introduced at one of the nitrogen atoms constituting the pyrazole ring and/or (where Q is a 4-pyridyl group) at the nitrogen atom of the 4-pyridyl group. Such a compound having a plurality of carboxylic residues introduced thereinto can be converted to a compound of formula (I) in accordance with the present invention by subsequent treatment with an alkali such as sodium hydroxide or potassium hydroxide.

In the above-described process (a) (i), the proportion of the carboxylic acid of formula (III) or its reactive derivative to the compound of formula (II) may generally be such that the carboxylic acid of formula (III) or its reactive derivative is used in an amount of at least 1 mole, preferably 1.5 to 10 moles, and more preferably 2 to 5 moles, per mole of the compound of formula (II). The base may generally be used in an amount of at least 1 mole and preferably 1 to 2 moles, per mole of the carboxylic acid of formula (III) or its reactive derivative.

In the above-described process (a) (ii), the reaction of the reactive derivative (e.g., phosphazo compound, phosphoroamidate compound, phosphoroamidide compound, isocyanate or thioisocyanate) of the amino compound of formula (II) with the carboxylic acid of formula (III) may generally be carried out in an inert organic solvent selected, for example, from ethers such as dioxane, tetrahydrofuran and dimethoxyethane; aromatic hydrocarbons such as benzene, toluene and xylene; halogenated hydrocarbons such as dichloromethane and chloroform; amides such as dimethylformamide and dimethylacetamide; and dimethyl sulfoxide. If necessary, this reaction may also be carried out in the presence of a base such as pyridine, 1,8-diazabicyclo[5.4.0]undec-7-ene ()BU), triethylamine, diisopropylethylamine, dimethylaminopyridine, pyridine or N-methylmorpholine. The reaction temperature may vary according to the type of the reactive derivative of the amino compound of formula (II) used. However, it is usually suitable to employ a temperature ranging from −10° C. to the reflux temperature of the reaction mixture and preferably from an ice-cold temperature to about 50° C.

The above-described reaction may usually be carried out by treating a free amino compound of formula (II) with phosphorus trichloride, tetraethyl pyrophosphate, phosgene or the like in the presence of the above-described base, and reacting the resulting Nu reactive derivative of the amino compound of formula (II) with a carboxylic acid of formula (III) without isolating the reactive derivative.

In the above-described process (b), the treatment with the Lawesson reagent of the compound of formula (I) in which Y is an oxygen atom may generally be carried out in an inert organic solvent such as an aromatic hydrocarbon (e.g., benzene, toluene or xylene). As the reaction temperature, it is usually suitable to employ a temperature ranging from 50° C. to the reflux temperature of the reaction mixture and preferably from 80° C. to the reflux temperature of the reaction mixture.

The Lawesson reagent used in process (b) is 2,4-bis(4-methoxyphenyl)-1,3-dithia-2,4-diphosphetane-2,4-disulfide. This Lawesson reagent may generally be used in an amount of at least 1 mole and preferably 1.05 to 1.5 moles, per mole of the compound of formula (I) in which Y is an oxygen atom.

The treatment with the organic sulfonic acid or its reactive derivative (e.g., acid chloride) in the above-described process (c) may generally be carried out in an inert organic solvent selected, for example, from ethers such as dioxane, tetrahydrofuran and dimethoxyethane; aromatic hydrocarbons such as benzene, toluene and xylene; halogenated hydrocarbons such as dichloromethane and chloroform; amides such as dimethylformamide and dimethylacetamide; and dimethyl sulfoxide. As the reaction temperature, it is usually suitable to employ a temperature ranging from 0° C. to the reflux temperature of the reaction mixture and preferably from an ice-cold temperature to the vicinity of room temperature.

It is preferable to treat the compound of formula (II) with a base (e.g., sodium hydride, sodium amide or potassium t-butoxide) in advance and thereby activate its amino group.

In process (c), the proportion of the organic sulfonic acid or its reactive derivative to the compound of formula (II) may generally be such that the organic sulfonic acid or its reactive derivative is used in an amount of at least 1 mole, preferably 1 to 2 moles, and more preferably 1.05 to 1.5 moles, per mole of the compound of formula (II).

In the above-described process (d), the treatment with a lower alkyl halide of the compound of formula (I) in which $R^1$ is a hydrogen atom may generally be carried out in an inert organic solvent selected, for example, from ethers such as dioxane, tetrahydrofuran and dimethoxyethane; amides such as dimethylformamide and dimethylacetamide; and aromatic hydrocarbons such as benzene and toluene, and in the presence of a base such as sodium hydride, sodium amide, potassium t-butoxide, potassium carbonate or sodium carbonate. The lower alkyl halides which can be used in this treatment include, for example, methyl iodide, ethyl iodide and isopropyl iodide. As the reaction temperature, it is usually suitable to employ a temperature ranging from 0° C. to the reflux temperature of the reaction mixture and preferably from an ice-cold temperature to the vicinity of room temperature.

The proportion of the lower alkyl halide to the compound of formula (I) in which $R^1$ is a hydrogen atom may generally be such that the lower alkyl halide is used in an amount of at least 1 mole and preferably 1.1 to 1.5 moles, per mole of the compound of formula (I).

In the above-described process (e), the treatment with a lower alkyl halide of the compound of formula (I) in which $R^2$ is a hydrogen atom may be carried out in the same manner as described above for process (d) involving the treatment with a lower alkyl halide of the compound of formula (I) in which $R^1$ is a hydrogen atom. Moreover, the treatment with an aralkyl halide (e.g., benzyl bromide or phenetyl iodide) of the compound of formula (I) in which $R^2$ is a hydrogen atom may be carried out under substantially the same reaction conditions as described above for process (d) involving the treatment with a lower alkyl halide of the compound of formula (I) in which $R^1$ is a hydrogen atom.

Where this reaction is carried out by using a compound of formula (I) in which both $R^1$ and $R^2$ are hydrogen atoms, it is advantageous to protect the nitrogen atoms of the pyrazole ring with protecting groups (e.g., pyrrolidine) in advance and eliminating the protecting groups after completion of the reaction.

In the reactions described herein, when the group represented by $R^3$ contains a group which may participate in the reaction (e.g., amino, hydroxyl or carboxyl), it is advantageous to protect this group suitably with an appropriate protecting group (e.g., benzyloxycarbonyl or t-butoxycarbonyl for amino; benzyl acetyl or methoxymethyl for hydroxyl; methyl ester or ethyl ester for carboxyl) in advance and eliminating the protecting groups after completion of the reaction.

The compounds of the above formula (I) or their salts, which have been formed in the above-described manner, may be isolated and purified from the reaction mixture by per se known techniques such as recrystallization, distillation, column chromatography and thin-layer chromatography.

The aminopyrazole derivatives of formula (I) or their salts in accordance with the present invention, which have been described above, have excellent p38MAP kinase inhibiting activities and are hence effective in hindering the production of TNF-α, IL-1, IL-6, COX-II and the like. Accordingly, they are useful as agents for the treatment of diseases associated with TNF-α, IL-1, IL-6 or COX-II, such as rheumatoid arthritis, multiple sclerosis, osteoarthritis, psoriasis, viral and bacterial infections, asthma, septic shock, IBD, Crohn's disease, Alzheimer's disease, diabetes, cachexia, osteoporosis, graft versus host disease, adult RDS, arteriosclerosis, gout, glomerulonephritis, congestive heart failure, ulcerative colitis, sepsis, cerebral malaria, restenosis, hepatitis, SLE, thrombosis, born resorption disease, chronic pulmonary inflammation disease, cardiac reperfuision injury, renal reperfusion injury, cancer, Reiter's syndrome, preterm labor, eczema, allograft rejection, stroke, fever, Behqet's disease, neuralgia, meningitis, sunburn, contact dermatitis, acute synovitis, spondylitis, muscle degeneration, angiogenesis, conjunctivitis, psoriatic arthritis, viral myocarditis, pancreatitis, glioblastoma, bleeding, joint inflammation, endotoxic shock, parasitic infections, tuberculosis, myocardial infarction, leprosy, diabetic retinopathy, IBS, transplant rejection, burns, bronchitis, ischemic heart disease, eclampsia, pneumonia, remission of swelling, low back pain, laryngopharyngitis, Kawasaki disease, myelopathy and atopic dermatitis.

The p38MAP kinase (p38MAPK) inhibiting activities of the compounds of formula (I) or their salts in accordance with the present invention can be measured in the following manner.

(1) Measurement of Inhibitory Activities against the Binding of p38MAPK

Inhibitory activities against the binding of p38MAPK were measured by use of the cytosol fraction of THP-1 cells which are cultured cells derived from the human monocyte. Specifically, THP-1 cells were suspended in a cell lysis buffer [20 mM Tris-HCl buffer (pH 7.4), 1 mM magnesium chloride, 1 mM PMSF (phenylmethylsulfonyl fluoride), 1 mM pepstatin A, 1 mM leupeptin, 10 mg/ml aprotinin] and then ultrasonicated in water. Thereafter, the suspension was centrifuged at 100,000×g for 1 hour, and the protein concentration of the resulting supernatant (cytosol fraction) was determined. This supernatant was diluted with the cell lysis buffer so that the protein concentration of the cytosol fraction was 1 mg/ml, dispensed, and stored at −80° C. till use.

The inhibitory activity of a test compound against the binding of p38MAPK was measured by incubating a mixture of the cytosol fraction (100 μg protein) of THP-1 cells and the test compound at 15° C. for 30 minutes, adding thereto 1.11 KBq of $^3$H-SB202190 (925 GBq/mmol; manufactured by Americium, England) as a radioligand, and reacting the resulting mixture at 15° C. for 3 hours. Non-specific binding was measured by adding 20 μM SB203580. In order to separate the free and bound types of radioligand, a charcoal solution (1% charcoal, 0.1% dextran T-70). The resulting mixture was cooled with ice for 15 minutes and then centrifuged (3,000 rpm, 10 minutes, 4° C.). After the addition of a liquid centiliter to the resulting supernatant, its radioactivity was measured with a liquid scintillation counter.

$^3$H-SB202190 used as a radioligand was 4-(4-fluorophenyl)-2-(4-hydroxy-3,5-di-$^3$H-phenyl)-5-(4-pyridyl)imidazole, and SB203580 added for the measurement of nonspecific binding was 4-(4-fluorophenyl)-2-(4-methanesulfonylphenyl)-5-(4-pyridyl)imidazole.

The results of measurement of compounds in accordance with the present invention are given below.

| Compound | IC$_{50}$ (nM) |
| --- | --- |
| Example 1 | 0.042 |
| Example 3 | 0.032 |
| Example 24 | 0.0023 |
| Example 35 | 0.0012 |
| Example 36 | 0.0061 |
| Example 38 | 0.035 |
| Example 41 | 0.0017 |
| Example 46 | 0.00043 |
| Example 48 | 0.026 |
| Example 49 | 0.083 |
| Example 51 | 0.00021 |
| Example 52 | 0.032 |
| Example 56 | 0.0000088 |
| Example 57 | 0.00084 |
| Example 60 | 0.057 |
| Example 67 | 0.050 |
| Example 69 | 0.00016 |
| Example 92 | 0.055 |
| Example 97 | 0.041 |
| Example 99 | 0.029 |
| Example 104 | 0.020 |
| Example 106 | 0.028 |
| Example 109 | 0.082 |

| Compound | IC$_{50}$ (nM) |
| --- | --- |
| Example 117 | 0.035 |
| Example 120 | 0.25 |
| Example 134 | 0.025 |

As described above, the compounds of the above formula (I) or salts thereof in accordance with the present invention have an excellent inhibitory activity against the binding of p38MAPK, and can hence be used as p38MAP kinase inhibitors for purposes of prophylaxis, therapy and treatment in human beings and other mammals by oral administration or parenteral administration (e.g., intramuscular injection, intravenous injection, intraarticular administration, intrarectal administration or percutaneous administration).

When the compounds of the present invention are used as drugs, they may be formed into any of various pharmaceutical preparations according to the intended purpose. These pharmaceutical preparations include solid preparations (e.g., tablets, hard capsules, soft capsules, granules, powders, fine subtilaes, pills, troches and patches), semisolid preparations (e.g., suppositories and ointments), and liquid preparations (e.g., injections, emulsions, suspensions, lotions and sprays). Nontoxic additives which can be used in the aforesaid pharmaceutical preparations include, for example, starch, gelatin, glucose, lactose, fructose, maltose, magnesium carbonate, talc, magnesium stearate, methylcellulose, carboxymethylcellulose and salts thereof, acacia, polyethylene glycol, alkyl esters of p-hydroxybenzoic acid, syrup, ethanol, propylene glycol, petrolatum, carbowax, glycerin, sodium chloride, sodium sulfite, sodium phosphate and citric acid. The aforesaid pharmaceutical preparations may also contain other therapeutically useful drugs.

The content of the compounds of the present invention in the aforesaid pharmaceutical preparations may vary according to the dosage form. Generally, it is desirable that solid and semisolid preparations contain the compounds of the present invention at a concentration of 0.1 to 50% by weight and liquid preparations contain them at a concentration of 0.05 to 10% by weight.

The dosage of the compounds of the present invention may vary widely according to the type of the mammal (including human being) to be treated, the route of administration, the severity of symptoms, the doctor's diagnosis, and the like. Generally, they may be administered in a daily dose of 0.02 to 10 mg/kg and preferably 0.1 to 2 mg/kg. However, it is a matter of course that they may be administered in doses less than the lower limit of the aforesaid range or greater than the upper limit thereof, depending on the severity of symptoms in the patient and the doctor's diagnosis. The aforesaid daily dose may be given at a time or in several divided doses.

EXAMPLE

The present invention is more specifically explained with reference to the following examples.

Example 1

Synthesis of 5-(4-fluorophenyl)-3-phenylacetylamino-4-(4-pyridyl)pyrazole 254 mg of 3-amino-5-(4-fluorophenyl)-4-(4-pyridyl)pyrazole was suspended in 20 ml of tetrahydrofuran, and 306 mg of triethylamine was added thereto. Then, 5 ml of a tetrahydrofuran solution containing 464 mg of phenylacetyl chloride was added dropwise thereto, followed by stirring at room temperature for 3 hours. After the addition of water, the reaction mixture was extracted with ethyl acetate. After the organic layer was washed with water and dried over anhydrous magnesium sulfate, the solvent was distilled off under reduced pressure. After the resulting residue was dissolved in a mixture composed of 20 ml of methanol and 2 ml of a 2 mol/L sodium hydroxide solution and stirred for 1 hour, the precipitated crystals were collected by filtration. Moreover, the crystals thus obtained were suspended in a mixture composed of 20 ml of methanol and 2 ml of a 2 mol/L sodium hydroxide solution, and heated under reflux for 5 hours. The reaction mixture was concentrated under reduced pressure and then purified by column chromatography using 20 g of silica gel [with an elution solvent comprising chloroform-methanol (30:1)]. Thus, 80 mg (22% yield) of the title compound was obtained as colorless crystals.

Melting point: 289.2–290.4° C. (n-hexane-ethyl acetate-ethanol)

$^1$H-NMR (DMSO-$d_6$) δ: 13.25 (bs, 1H), 9.93 (bs, 1H), 8.34 (d, J=5.9 Hz, 2H), 7.50–7.06 (m, 9H), 7.01 (d, J=5.9 Hz, 2H), 3.56 (s, 2H)

IR (KBr) ν max: 1694, 1600, 1586 cm$^{-1}$

Mass, m/e: 372 (M$^+$), 91 (base)

The compounds of the following Examples 2–21 were synthesized in substantially the same manner as in Example 1.

Example 2

5-(4-Fluorophenyl)-3-(3-phenylpropionylamino)-4-(4-pyridyl)pyrazole

Melting point: 253.5–255.1° C.

$^1$H-NMR (DMSO-$d_6$) δ: 13.20 (bs, 1H), 9.68 (bs, 1H), 8.42 (d, J=5.9 Hz, 2H), 7.50–6.93 (m, 9H), 7.06 (d, J=5.9 Hz, 2H), 3.00–2.70 (m, 2H), 2.70–2.35 (m, 2H)

IR (KBr) ν max: 3368, 1676, 1602, 1590 cm$^{-1}$

Mass, m/e: 386 (M$^+$), 254 (base)

Example 3

5-(4-Fluorophenyl)-3-(4-methoxyphenylacetylanino)-4-(4-pyridyl)pyrazole

Melting point: 265.1–266.2° C.

$^1$H-NMR (DMSO-$d_6$) δ:13.21 (bs, 1H), 9.75 (bs, 1H), 8.45–8.15 (m, 2H), 7.50–6.65 (m, 10H), 3.75 (s, 3H), 3.46 (s, 2H)

IR (KBr) ν max: 3300, 1678, 1608, 1588, 1250 cm$^{-1}$

Mass, m/e: 402 (M$^+$), 121 (base)

Example 4

3-(3,4-Dichlorophenylacetylamino)-5-(4-fluorophenyl)-4-(4-pyridyl)pyrazole

Melting point: 285.7–286.7° C.

$^1$H-NMR (DMSO-$d_6$) δ: 13.27 (bs, 1H), 9.92 (bs, 1H), 8.50–8.15 (m, 2H), 7.70–6.90 (m, 9H), 3.59 (s, 2H)

IR (KBr) ν max: 1674, 1606, 1590 cm$^{-1}$

Mass, m/e: 444 (M$^+$+4), 442 (M$^+$+2), 440 (M$^+$), 254 (base)

Example 5

5-(4-Fluorophenyl)-3-(2-phenylpropionylamino)-4-(4-pyridyl)pyrazole

Melting point: 240.6–241.0° C.

$^1$H-NMR (DMSO-$d_6$) δ: 13.21 (bs, 1H), 9.75 (bs, 1H), 8.40–8.10 (m, 2H), 7.45–7.00 (m, 9H), 6.89 (d, J=6.2 Hz, 2H), 3.95–3.60 (m, 1H), 1.35 (d, J=6.2 Hz, 3H)

IR (KBr) ν max: 3264, 1658, 1606, 1508 cm$^{-1}$

Mass, m/e: 386 (M$^+$), 105 (base)

Example 6

3-(4-Chlorophenylacetylamino)-5-(4-fluorophenyl)-4-(4-pyridyl)pyrazole

Melting point: 273.2–277.3° C.

$^1$H-NMR (DMSO-$d_6$) δ: 13.25 (bs, 1H), 10.13 (bs, 0.4H), 9.85 (bs, 0.61), 8.31 (bs, 2H), 7.5–6.9 (m, 12H), 3.7–3.4 (m, 2H)

IR (KBr) ν max: 1692, 1602, 1514, 1228, 838 cm$^{-1}$

Mass, m/e: 406 (M$^+$), 254 (base), 125

Example 7

5-(4-Fluorophenyl)-3-(4-methylphenylacetylamino)-4-(4-pyridyl)pyrazole

Melting point: 262.8–264.7° C.

$^1$H-NMR (DMSO-$d_6$) δ: 13.26 (bs, 1H), 9.82 (bs, 1H), 8.33 (d, J=5 Hz, 2H), 7.45–7.06 (m, 8H), 7.01 (d, J=5 Hz, 2H), 3.50 (s, 2H), 2.29 (s, 3H)

IR (KBr) ν max: 1690, 1602, 1512, 1224, 838 cm$^{-1}$

Mass, m/e: 386 (M$^+$), 254, 105 (base)

Example 8

5-(4-Fluorophenyl)-4-(4-pyridyl)-3-(4-trifluoromethylphenylacetylamino)pyrazole

Melting point: 282.1–288.4° C.

$^1$H-NMR (DMSO-$d_6$) δ: 13.26 (bs, 1H), 9.96 (bs, 1H), 8.34 (bs, 2H), 7.70–7.10 (m, 8H), 7.01 (bd, 2H), 3.67 (s, 2H)

IR (KBr) ν max: 1692, 1608, 1510, 1326, 1160, 1122, 832 cm$^{-1}$

Mass, m/e: 440 (M$^+$), 254 (base), 159

Example 9

3-Phenylacetylamino-5-phenyl-4-(4-pyridyl)pyrazole

Melting point: 257.3–264.1° C.

$^1$H-NMR (DMSO-$d_6$) δ: 13.23 (bs, 1H), 9.82 (bs, 1H), 8.30 (bd, J=4.4 Hz, 2H), 7.5–7.1 (m, 10H), 7.01 (d, J=5.9 Hz, 2H), 3.55 (s, 2H)

IR (KBr) ν max: 1694, 1604, 772, 698 cm$^{-1}$

Mass, m/e: 354 (M$^+$), 236, 91 (base)

Example 10

5-(4-Fluorophenyl)-4-(4-quinolyl)-3-phenylacetylaminopyrazole

Melting point: 273.4–275.3° C. (n-hexane-ethanol)

$^1$H-NMR (DMSO-$d_6$) δ: 13.39 (bs, 1H), 10.03 (bs, 0.4H), 9.76 (bs, 0.6H), 8.87 (d, J=4.4 Hz, 0.8H), 8.74 (d, J=4.4 Hz, 1.21), 8.15–6.65 (m, 13H), 3.49, 3.35 (s, 2H)

IR (KBr) ν max: 1682, 1608, 1512, 1230, 842 cm$^{-1}$

Mass, m/e: 422 (M$^+$), 304, 91 (base)

Example 11

5-(4-Fluorophenyl)-4-(4-pyridyl)-3-(2-thienylacetylamino)pyrazole

Melting point: 264.6–268.3° C. (n-hexane-ethyl acetate) (decomp.)

$^1$H-NMR (CDCl$_3$) δ: 8.46 (dd-like, 2H), 7.61–7.46 (m, 3H), 7.21–6.88 (m, 8H), 4.65 (s, 2H)

IR (KBr) ν max: 1660, 1608, 1232 cm$^{-1}$

Mass, m/e: 378 (M$^+$), 97 (base)

Example 12

5-(4-Fluorophenyl)-3-(2-phenyl-n-butyrylamino)-4-(4-pyridyl)pyrazole

Melting point: 266.8–268.4° C.

$^1$H-NMR (DMSO-d$_6$) δ: 13.21 (bs, 1H), 9.89 (bs, 1H), 8.23 (d, J=4.6 Hz, 2H), 7.44–7.10 (m, 9H), 6.90 (dd, J=1.5, 4.6 Hz, 2H), 3.52 (t, J=7.3 Hz, 1H), 2.16–1.47 (m, 2H), 0.80 (t, J=7.3 Hz, 3H)

IR (KBr) ν max: 3272, 2864, 1658, 1518, 1504, 1230, 830 cm$^{-1}$

Mass, m/e: 400 (M$^+$), 91 (base)

Example 13

3-Benzoylamino-5-(4-fluorophenyl)-4-(4-pyridyl)pyrazole

Melting point: 270.5–276.1° C.

$^1$H-NMR (CDCl$_3$) δ: 8.50 (dd, J=1.5, 4.6 Hz, 2H), 7.89–6.94 (m, 11H)

IR (KBr) ν max: 1674, 1601, 1515cm$^{-1}$

Mass, m/e: 358 (M$^+$), 105 (base)

Example 14

5-(4-Fluorophenyl)-3-hydroxyacetylamino-4-(4-pyridyl)pyrazole

Melting point: 264–266° C.

$^1$H-NMR (DMSO-d$_6$) δ: 13.5–13.3 (bs, 1H), 9.6–9.3 (bs, 1H), 8.59 (dd, J=1.5, 4.6 Hz, 2H), 7.5–7.0 (m, 6H), 5.7–5.4 (bs, 1H), 3.94 (bs, 2H)

IR (KBr) ν max: 3250, 1608, 1510 cm$^{-1}$

Mass, m/e: 312 (M$^+$, base)

Example 15

5-(4-Fluorophenyl)-3-methoxyacetylamino-4-(4-pyridyl)pyrazole

Melting point: 246–248° C.

$^1$H-NMR (DMSO-d$_6$) δ: 13.5–13.1 (bs, 1H), 9.8–9.4 (bs, 1H), 8.46 (dd, J=1.3, 4.6 Hz, 2H), 7.5–7.0 (m, 6H), 3.93 (s, 2H), 3.30 (s, 3H)

IR (KBr) ν max: 3200, 1672, 1608, 1512 cm$^{-1}$

Mass, m/e: 326 (M$^+$, base)

Example 16

Sodium 3-[[5-(4-fluorophenyl)-4-(4-pyridyl)]pyrazol-3-yl]aminocarbonylpropionate Melting point: 196–200° C.

$^1$H-NMR (CD$_3$OD) δ: 8.44 (dd, J=1.5, 4.6 Hz, 2H), 7.5–7.0 (m, 6H), 2.55 (m, 4H)

Example 17

5-(4-Fluorophenyl)-3-propionylamino-4-(4-pyridyl)pyrazole

Melting point: 272.0–275.0° C. (n-hexane-ethyl acetate)

$^1$H-NMR (DMSO-d$_6$) δ: 13.22 (bs, 1H), 9.50 (bs, 1H), 8.50–8.43 (m, 2H), 7.49–7.19 (m, 4H), 7.12 (dd, J=1.5, 4.4 Hz, 2H), 2.22 (q, J=7.5 Hz, 2H), 1.00 (t, J=7.3 Hz, 3H)

IR (KBr) ν max: 1688, 1608, 1510, 1222, 836 cm$^{-1}$

Mass, m/e: 310 (M$^+$), 254, 57 (base)

Example 18

5-(4-Fluorophenyl)-3-isobutyrylamino-4-(4-pyridyl)pyrazole

Melting point: 291.1–294.0° C. (n-hexane-ethyl acetate)

$^1$H-NMR (DMSO-d$_6$) δ: 13.22 (bs, 1H), 9.48 (bs, 1H), 8.50–8.41 (m, 2H), 7.48–7.02 (m, 6H), 1.01 (d, J=6.6 Hz, 6H)

IR (KBr) ν max: 1666, 1604, 1508, 1216, 836 cm$^{-1}$

Mass, m/e: 324 (M$^+$), 254 (base)

Example 19

5-(4-Fluorophenyl)-3-isovalerylamino-4-(4-pyridyl)pyrazole

Melting point: 291.1–294.0° C. (n-hexane-ethyl acetate)

$^1$H-NMR (DMSO-d$_6$) δ: 13.21 (bs, 1H), 9.50 (bs, 1H), 8.47–8.41 (m, 2H), 7.46–7.03 (m, 6H), 2.20–1.95 (m, 2H), 1.20–0.65 (m, 7H)

IR (KBr) ν max: 1684, 1604, 1514, 1238, 838 cm$^{-1}$

Mass, m/e: 338 (M$^+$), 254, 57 (base)

Example 20

5-(4-Fluorophenyl)-4-(4-pyridyl)-3-valerylaminopyrazole

Melting point: 273.7–275.8° C. (n-hexane-ethyl acetate)

$^1$H-NMR (DMSO-d$_6$) δ: 13.21 (bs, 1H), 9.56 (bs, 1H), 8.46 (dd, J=1.5, 4.4 Hz, 2H), 7.48–7.02 (m, 4H), 7.12 (dd, J=1.5, 4.4 Hz, 2H), 2.24–2.15 (m, 2H), 1.51–1.22 (m, 4H), 0.85 (t, J=5.7 Hz, 3H)

IR (KBr) ν max: 1680, 1606, 1510, 1238, 836 cm$^{-1}$

Mass, m/e: 338 (M$^+$), 254 (base)

Example 21

5-(4-Fluorophenyl)-4-(4-pyridyl)-3-pivaloylaminopyrazole

Melting point: 217.9–220.6° C. (n-hexane-ethyl acetate)

$^1$H-NMR (DMSO-d$_6$) δ: 13.23 (bs, 1H), 9.16 (bs, 1H), 8.44 (dd, J=1.3, 4.6 Hz, 2H), 7.48–7.16 (m, 4H), 7.11 (dd, J=1.5, 4.4 Hz, 2H), 1.14 (s, 9H)

IR (KBr) ν max: 1664, 1606, 1512, 1224, 836 cm$^{-1}$

Mass, m/e: 338 (M$^+$), 57 (base)

Example 22

Synthesis of 5-(4-fluorophenyl)-4-(4-pyridyl)-3-trifluoroacetylaminopyrazole 254 mg of 3-amino-5-(4-fluorophenyl)-4-(4-pyridyl)pyrazole and 0.30 ml of triethylamine were dissolved in 20 ml of tetrahydrofuran. While this solution was being cooled with ice, 400 mg of trifluoroacetic anhydride was added thereto with stirring. The resulting mixture was stirred at room temperature for 2 hours. After the addition of water, the reaction mixture was extracted with chloroform. After the organic layer was dried over anhydrous magnesium sulfate, the solvent was distilled off under reduced pressure. The resulting residue was purified by column chromatography using 50 g of silica gel [with an elution solvent comprising chloroform-methanol (30:1)]. Thus, 220 mg (63% yield) of the title compound was obtained as colorless crystals.

Melting point: 260.1–265.2° C. (n-hexane-ethyl acetate)

$^1$H-NMR (DMSO-$d_6$) δ: 13.55 (bs, 1H), 11.31 (bs, 1H), 8.46 (dd, J=1.5, 4.4 Hz, 2H), 7.50–7.07 (m, 6H)

IR (KBr) ν max: 1742, 1608, 1512, 1224, 838 cm$^{-1}$

Mass, m/e: 350 (M$^+$, base), 254

Example 23

Synthesis of 3-cyclohexylacetylamino-5-(4-fluorophenyl)-4-(4-pyridyl)pyrazole 220 mg of cyclohexylacetic acid was dissolved in 10 ml of tetrahydrofuran. While this solution was being cooled at −10° C., 160 mg of N-methylmorpholine and 220 mg of isobutyl chloroformate were added thereto with stirring. The resulting mixture was stirred for 15 minutes. After the addition of 127 mg of 3-amino-5-(4-fluorophenyl)-4-(4-pyridyl)pyrazole, the mixture was stirred for 30 minutes and then stirred at room temperature for 4 days. After the addition of water, the reaction mixture was extracted with ethyl acetate. After the organic layer was dried over anhydrous magnesium sulfate, the solvent was distilled off under reduced pressure. After the resulting residue was dissolved in 10 ml of methanol, 1 ml of 2N sodium hydroxide was added thereto, followed by stirring at room temperature for 90 minutes. Then, the solvent was distilled off under reduced pressure. After the addition of water, this mixture was extracted with ethyl acetate. After the organic layer was dried over anhydrous magnesium sulfate, the solvent was distilled off under reduced pressure. The resulting residue was purified by column chromatography using 30 g of silica gel [with an elution solvent comprising chloroform-methanol (30:1)]. Thus, 55 mg (29% yield) of the title compound was obtained as colorless crystals.

Melting point: 296.3–299.9° C. (n-hexane-ethyl acetate)

$^1$H-NMR (DMSO-$d_6$) δ: 13.20 (bs, 1H), 9.55 (bs, 1H), 8.48–8.42 (m, 2H), 7.46–7.04 (m, 4H), 7.12 (dd, J=1.5, 4.4 Hz, 2H), 2.09 (d, J=7.0 Hz, 2H), 1.73–1.47 (m, 5H), 1.19–0.78 (m, 6H)

IR (KBr) ν max: 1680, 1606, 1512, 1234, 836 cm$^{-1}$

Mass, m/e: 378 (M$^+$), 254, 55 (base)

Example 24

Synthesis of 3-(2-chlorophenylacetylamino)-5-(4-fluorophenyl)-4-(4-pyridyl)pyrazole 150 mg of 3-amino-5-(4-fluorophenyl)-4-(4-pyridyl)pyrazole was dispersed in 6 ml of pyridine. While this dispersion was being cooled on a salt-ice bath, 122 mg of phosphorus trichloride was added thereto with stirring. After the resulting mixture was stirred at the same temperature for 25 minutes, 335 mg of 2-chlorophenylacetic acid was added thereto, followed by stirring at room temperature for 20 hours. After the pyridine was distilled off under reduced pressure, the residue was extracted with methanol and chloroform. After the organic layer was washed with water and dried over anhydrous magnesium sulfate, the solvent was distilled off under reduced pressure. The resulting residue was purified by column chromatography using 80 g of silica gel [with an elution solvent comprising chloroform-methanol (30:1)]. Thus, 101 mg (42% yield) of the title compound was obtained.

Melting point: 238.8–240.1° C. (n-hexane-ethanol)

$^1$H-NMR (DMSO-$d_6$) δ: 13.26 (bs, 1H), 9.88 (bs, 1H), 8.43 (d, J=6 Hz, 2H), 7.5–7.2 (m, 8H), 7.13 (d, J=6 Hz, 2H), 3.75 (s, 2H)

IR (KBr) ν max: 1664, 1608, 1506, 1228, 838 cm$^{-1}$

Mass, m/e: 406 (M$^+$), 254, 125 (base)

The compounds of the following Examples 25–33 were synthesized in substantially the same manner as in Example 24.

Example 25

3-(3-Chlorophenylacetylamino)-5-(4-fluorophenyl)-4-(4-pyridyl)pyrazole

Melting point: 249.7–250.8° C. (n-hexane-ethanol)

$^1$H-NMR (DMSO-$d_6$) δ: 13.26 (bs, 1H), 10.17 (bs, 0.21), 9.90 (bs, 0.8H), 8.32 (d, J=6 Hz, 2H), 7.5–7.1 (m, 8H), 7.00 (d, J=6 Hz, 2H), 3.56 (s, 2H)

IR (KBr) ν max: 1694, 1600, 1512, 1222, 838 cm$^{-1}$

Mass, m/e: 406 (M$^+$), 254 (base), 125

Example 26

5-(4-Fluorophenyl)-3-(4-fluorophenylacetylamino)-4-(4-pyridyl)pyrazole

Melting point: 259.4–261.2° C. (n-hexane-ethanol)

$^1$H-NMR (DMSO-$d_6$) δ: 13.25 (bs, 1H), 10.12 (bs, 0.2H), 9.86 (bs, 0.8H), 8.30 (bd, 2H), 7.5–6.7 (m, 10H), 3.61 (s, 0.4H), 3.53 (s, 1.6H)

IR (KBr) ν max: 1692, 1602, 1506, 1224, 840 cm$^{-1}$

Mass, m/e: 390 (M$^+$), 254, 109 (base)

Example 27

5-(4-Fluorophenyl)-3-(4-nitrophenylacetylamino)-4-(4-pyridyl)pyrazole

Melting point: 299.3–302.3° C. (n-hexane-tetrahydrofuran-ethanol)

$^1$H-NMR (DMSO-$d_6$) δ: 13.26 (bs, 1H), 10.00 (bs, 1H), 8.36 (bd, 2H), 8.17 (d, J=8.6 Hz, 2H), 7.65–7.10 (m, 6H), 7.03 (d, J=4.8 Hz, 2H), 3.74 (s, 2H)

IR (KBr) ν max: 1692, 1606, 1512, 1346, 1220, 840 cm$^{-1}$

Mass, m/e: 417 (M$^+$), 254 (base), 136

Example 28

5-(4-Fluorophenyl)-4-(4-pyridyl)-3-(3-thienylacetylamino)pyrazole

Melting point: 279.6–282.9° C. (decomp.)

$^1$H-NMR (DMSO-$d_6$) δ: 13.22 (bs, 1H), 9.84 (bs, 1H), 8.36 (dd-like, 2H), 7.50–7.11 (m, 9H), 7.00 (dd-like, 2H), 3.58 (s, 2H)

IR (KBr) ν max: 1660, 1624, 1600, 1518, 1508, 1494, 1222, 842, 700 cm$^{-1}$

Mass, m/e: 378 (M$^+$), 97 (base)

Example 29

5-(4-Fluorophenyl)-4-(4-pyridyl)-3-(4-pyridylacetylamino)pyrazole

Melting point: 248.3–251.8° C. (decomp.)
$^1$H-NMR (CDCl$_3$) δ: 8.55–8.37 (m, 4H), 7.40–7.14 (m, 6H), 7.10–6.92 (m, 4H), 3.71 (s, 2H)
IR (KBr) ν max: 1660, 1608, 1232 cm$^{-1}$
Mass, m/e: 373 (M$^+$), 120 (base)

Example 30

3-(1-Methyl-2-pyrrolylacetylamino)-5-(4-fluorophenyl)-4-(4-pyridyl)pyrazole

Melting point: 238.7–239.9° C. (n-hexane-ethyl acetate)
$^1$H-NMR (CDCl$_3$) δ: 8.48 (dd, J=1.7, 4.5 Hz, 2H), 7.96 (bs, 1H), 7.45–6.90 (m, 6H), 6.78 (dd, J=1.7, 4.5 Hz, 2H), 6.71–6.65 (m, 1H), 6.19–6.08 (m, 1H), 3.75 (s, 2H), 3.53 (s, 3H)
IR (KBr) ν max: 1592, 1512, 1220, 838 cm$^{-1}$
Mass, m/e: 375 (M$^+$), 94 (base)

Example 31

5-(4-Fluorophenyl)-3-(2,3,4,5,6-pentafluorophenylacetylamino)-4-(4-pyridyl)pyrazole Melting point: 325° C. or above (n-hexane-ethanol)
$^1$H-NMR (DMSO-d$_6$) δ: 13.3 (bs, 1H), 10.1 (1b, 1H1), 8.45 (dd, J=1.3, 4.8 Hz, 2H), 7.5–7.2 (m, 4H), 7.11 (dd, J=1.3, 4.8 Hz, 2H), 3.79 (s, 2H)
IR (KBr) ν max: 3216, 1674, 1606, 1512, 1002 cm$^{-1}$
Mass, m/e: 462 M$^+$), 254 (base)

Example 32

3-Diphenylacetylamino-5-(4-fluorophenyl)-4-(4-pyridyl)pyrazole

Melting point: 266.5–269.2° C.
$^1$H-NMR (DMSO-d$_6$) δ: 8.26 (d, J=5.9 Hz, 2H), 7.45–7.21 (m, 14H), 6.96 (d, J=5.9 Hz, 2H), 5.10 (s, 1H)
IR (KBr) ν max: 3228, 1668, 1608, 1500, 1232, 836 cm$^{-1}$
Mass, m/e: 448 (M$^+$), 167 (base)

Example 33

3-(α,α-Dimethylphenylacetylamino)-5-(4-fluorophenyl)-4-(4-pyridyl)pyrazole

Melting point: 239.1–241.5° C.
$^1$H-NMR (DMSO-d$_6$) δ: 8.34 (dd, J=1.8 Hz, 4.4 Hz, 2H), 7.36–6.97 (m, 11H), 1.43 (d, J=11.6 Hz, 6H)
IR (KBr) ν max: 3304, 1666, 1604, 1508, 1236, 834 cm$^{-1}$
Mass, m/e: 400 (M$^+$), 119 (base)

Example 34

Synthesis of 5-amino-3-(4-fluorophenyl)-1-methyl-4-(4-pyridyl)pyrazole (a) Synthesis of 3-(4-fluorophenyl)-3-oxo-2-(4-pyridyl)propionitrile 32 g of 4-pyridylacetonitrile and 86 g of 2,5-dioxopyrrolidinyl 4-fluorobenzoate were dissolved in 1.3 L of dimethylformamide. After the addition of 164 g of potassium carbonate, the resulting mixture was stirred at room temperature for a day. After the reaction mixture was filtered through cerite, the filtrate was concentrated under reduced pressure. After water was added to the residue, this solution was neutralized with an aqueous solution of hydrochloric acid. The precipitated crystals were collected by filtration, washed with diethyl ether, and then dried in a stream of air to obtain 67 g (103% yield) of the title compound.

Melting point: 220.0–223.0° C. (decomp.)
$^1$H-NMR (CD$_3$OD) δ: 8.23–7.97 (m, 4H), 7.80–7.61 (m, 2H), 7.12 (t, J=8.9 Hz, 2H)
IR (KBr) ν max: 2180, 1636, 1608, 1542, 1492, 1408, 1374, 1342, 1222, 1202, 1156, 830 cm.$^{-1}$
Mass, m/e: 240 (M$^+$), 123 (base)

(b) Synthesis of 1-methyl-t-butyl carbazate 26 g of methylhydrazine and 23 g of sodium hydroxide were dissolved in 500 ml of methanol. While this solution was being cooled with ice, 500 ml of a methanolic solution containing 123 g of di-t-butyl dicarbonate was added dropwise thereto over a period of 2 hours. Moreover, the reaction mixture was stirred at room temperature for 2 hours. After the precipitate formed in the reaction mixture was separated by filtration through cerite, the filtrate was concentrated under reduced pressure. After 500 ml of water added to the resulting oily residue, the resulting mixture was neutralized with an aqueous solution of ammonium chloride and extracted with dichloromethane. After the organic layer was dried over anhydrous magnesium sulfate, the solvent was distilled off under reduced pressure to obtain 79 g (97% yield) of the title compound.

Oily matter
$^1$H-NMR (CDCl$_3$) δ: 4.06 (br, 2H), 3.05 (s, 3H), 1.47 (s, 9H)
IR (neat) ν max: 1694, 1365, 1154 cm$^-$ (c) Synthesis of 5-amino-3-(4-fluorophenyl)-1-methyl-4-(4-pyridyl)pyrazole 10 ml of phosphorus oxychloride was added to 2.0 g of 3-(4-fluorophenyl)-3-oxo-2-(4-pyridyl)propionitrile, followed by stirring in an oil bath at 100° C. for 1 hour. After the reaction mixture was concentrated under reduced pressure, the resulting residue was dissolved in 150 ml of ethanol. Then, 3.5 g of 1-methyl-t-butyl carbazate was added thereto, followed by heating under reflux for 1.5 hours. Thereafter, 3 ml of trifluoroacetic acid was added thereto, followed by stirring in an oil bath at 100° C. After being allowed to cool, the reaction mixture was concentrated under reduced pressure. After the addition of water, the resulting mixture was neutralized with sodium bicarbonate and extracted with chloroform. After the organic layer was dried over anhydrous magnesium sulfate, the solvent was distilled off under reduced pressure. The resulting oily residue was purified by column chromatography using 80 g of silica gel [with an elution solvent comprising chloroform-methanol (50:1–20:1)]. Thus, 1.5 g (62% yield) of the title compound was obtained.

Melting point: 155.2–157.9° C.
$^1$H-NMR (CDCl$_3$) δ: 8.53 (dd, J=1.5, 4.4 Hz, 2H), 7.50–6.83 (m, 4H), 7.08 (dd, J=1.5, 4.4 Hz, 2H), 3.77 (bs, 2H), 3.77 (s, 3H)
IR (KBr) ν max: 1598, 1212
Mass, m/e: 268 (M$^+$, base)

Example 35

Synthesis of 5-(2,5-difluorophenylacetylamino)-3-(4-fluorophenyl)-1-methyl-4-(4-pyridyl)pyrazole 268 mg of 5-amino-3-(4-fluorophenyl)-1-methyl-4-(4-pyridyl)pyrazole and 258 mg of 2,5-difluorophenylacetic acid were dissolved in 10 ml of pyridine, and 0.09 ml of phosphorus trichloride was added dropwise thereto at room temperature. After being stirred at room temperature overnight, the reaction mixture was concentrated. After the addition of a 2N aqueous solution of NaOH, the resulting mixture was extracted with chloroform. After the organic layer was dried over anhydrous magnesium sulfate, the solvent was distilled off under reduced pressure. The resulting crystalline residue was washed with diethyl ether to obtain 247 mg (56% yield) of the title compound.

Melting point: 207.0–208.0° C.

$^1$H-NMR (CDCl$_3$) δ: 8.43 (dd, J=1.5, 4.6 Hz, 2H), 7.62–6.87 (m, 10H), 3.78 (s, 3H), 3.74 (d-like, 2H)

IR (KBr) ν max: 1606, 1498, 1220 m$^{-1}$

Mass, m/e: 422 (M$^+$), 268 (base)

The compounds of the following Examples 36–82 were synthesized in substantially the same manner as in Example 35.

Example 36

5-(2-Chloro-6-fluorophenylacetylamino)-3-(4-fluorophenyl)-1-methyl-4-(4-pyridyl)pyrazole Melting point: 216.9–224.6° C.

$^1$H-NMR (CDCl$_3$) δ: 8.60–8.42 (m, 2H), 7.42–6.87 (m, 10H), 3.95 (d-like, 2H), 3.81 (s, 3H)

IR (KBr) ν max: 1676, 1606, 1452 cm$^{-1}$

Mass, m/e: 438 (M$^+$), 268 (base)

Example 37

5-(3,4-Dichlorophenylacetylamino)-3-(4-fluorophenyl)-1-methyl-4-(4-pyridyl)pyrazole Melting point: 205.1–207.0° C.

$^1$H-NMR (CDCl$_3$) δ: 8.40 (dd, J=1.3, 4.6 Hz, 2H), 7.49–6.81 (m, 10H), 3.75 (s, 3H), 3.69 (s, 2H)

IR (KBr) ν max: 1670, 1602, 1523, 1472, 1448, 1219 cm$^{-1}$

Mass, m/e: 454 (M$^+$), 268 (base)

Example 38

5-(2,6-Dichlorophenylacetylamino)-3-(4-fluorophenyl)-1-methyl-4-(4-pyridyl)pyrazole Melting point: 252.5–256.7° C. (n-hexane-ethyl acetate)

$^1$H-NMR (CDCl$_3$) δ: 8.48 (d, J=3.5 Hz, 2H), 7.50–6.80 (m, 9H), 4.14 (s, 2H), 3.82 (s, 3H)

IR (KBr) ν max: 1678, 1608, 1438, 1224 cm$^{-1}$

Mass, m/e: 454 (M$^+$), 268 (base)

Example 39

5-(2-Chloro-4-fluorophenylacetylamino)-3-(4-fluorophenyl)-1-methyl-4-(4-pyridyl)pyrazole Melting point: 229.0–232.7° C. (n-hexane-ethyl acetate)

$^1$H-NMR (CDCl$_3$) δ: 8.47 (dd, J=1.5, 4.6 Hz, 2H), 7.46–6.80 (m, 9H), 3.83 (s, 2H), 3.80 (s, 3H)

IR (KBr) ν max: 1694, 1606, 1494, 1240 cm$^{-1}$

Mass, m/e: 438 (M$^+$), 268 (base)

Example 40

5-(2,4-Difluorophenylacetylamino)-3-(4-fluorophenyl)-1-methyl-4-(4-pyridyl)pyrazole Melting point: 225.5–228.3° C. (n-hexane-ethyl acetate)

$^1$H-NMR (CDCl$_3$) δ: 8.45 (dd, J=1.5, 4.6 Hz, 2H), 7.50–6.70 (m, 9H), 3.78 (s, 3H), 3.73 (s, 2H)

IR (KBr) ν max: 1676, 1604, 1506, 1222 cm$^{-1}$

Mass, m/e: 422 (M $^+$), 268 (base)

Example 41

5-(2,4-Dichlorophenylacetylamino)-3-(4-fluorophenyl)-1-methyl-4-(4-pyridyl)pyrazole Melting point: 224.3–225.4° C.

$^1$H-NMR (CDCl$_3$) δ: 8.45 (dd, J=1.5, 4.4 Hz, 2H), 7.45–6.83 (m, 9H), 3.83 (s, 2H), 3.79 (s, 3H)

IR (KBr) ν max: 3272, 1678, 1602, 1570, 1508, 1200, 846, 826 cm$^{-1}$

Mass, m/e: 456 (M$^+$+2), 454 M$^+$), 268 (base)

Example 42

5-(3,4-Dimethoxyphenylacetylamino)-3-(4-fluorophenyl)-1-methyl-4-(4-pyridyl)pyrazole Melting point: 128.1–129.6° C.

$^1$H-NMR (CDCl$_3$) δ: 8.45 (dd, J=1.5, 4.4 Hz, 2H), 7.41–7.22 (m, 2H), 7.20–6.68 (m, 8H), 3.89 (s, 3H), 3.81 (s, 3H), 3.76 (s, 3H), 3.69 (s, 2H)

IR (KBr) ν max: 1676, 1606, 1516, 1448, 1262, 1224 cm$^{-1}$

Mass, m/e: 446 (M$^+$), 151 (base)

Example 43

3-(4-Fluorophenyl)-1-methyl-5-(3,4-methylenedioxyphenylacetylamino)-4-(4-pyridyl)pyrazole Melting point: 113.6–116.5° C.

$^1$H-NMR (CDCl$_3$) δ: 8.47 (dd, J=1.5, 4.4 Hz, 2H), 7.42–7.26 (m, 2H), 7.10–6.63 (m, 8H), 6.00 (s, 2H), 3.77 (s, 3H), 3.65 (s, 2H)

IR (KBr) ν max: 1603, 1502, 1489, 1447, 1262, 1246 cm$^{-1}$

Mass, m/e: 430 (M$^+$), 135 (base)

Example 44

5-(3,4-Dimethoxyphenylacetylamino)-3-(4-fluorophenyl)-1-methyl-4-(4-pyridyl)pyrazole Melting point: 174.4–180.3° C.

$^1$H-NMR (CDCl$_3$) δ: 8.44 (dd, J=1.7, 4.5 Hz, 2H), 7.41–7.26 (m, 2H), 7.09–6.87 (m, 5H), 6.40 (s, 3H), 3.76 (s, 9H), 3.67 (s, 2H)

IR (KBr) ν max: 1602, 1448, 1207, 1157 cm$^{-1}$

Mass, m/e: 446 (M$^+$), 151 (base)

Example 45

5-(3,5-Ditrifluoromethylphenylacetylamino)-3-(4-fluorophenyl)-1-methyl-4-(4-pyridyl)pyrazole Melting point: 228.3–230.6° C.

$^1$H-NMR (CDCl$_3$) δ: 8.40 (dd-like, 2H), 7.86–7.61 (m, 3H), 7.40–7.26 (m, 2H), 7.12–6.87 (m, 4H), 3.88 (s, 2H), 3.77 (s, 3H)

IR (KBr) ν max: 1680, 1606, 1526, 1380, 1280, 1222, 1176 cm$^{-1}$

Mass, m/e: 522 (M$^+$), 268 (base)

Example 46

5-(2,6-Difluorophenylacetylamino)-3-(4-fluorophenyl)-1-methyl-4-(4-pyridyl)pyrazole Melting point: 239.9–242.5° C.
$^1$H-NMR (CDCl$_3$) δ: 8.42 (dd, J=1.7, 4.5 Hz, 2H), 7.46–6.84 (m, 10H), 3.79 (s, 5H)
IR (KBr) ν max: 1694, 1606, 1470, 1014 m$^{-1}$
Mass, m/e: 422 (M$^+$), 127 (base)

Example 47

5-(3,4-Difluorophenylacetylamio)-3-(4-fluorophenyl)-1-methyl-4-(4-pyridyl)pyrazole Melting point: 214.2–217.7° C.
$^1$H-NMR (CDCl$_3$) δ: 8.44 (dd, J=1.4, 4.5 Hz, 2H), 7.44–6.84 (m, 10H), 3.76 (s, 3H), 3.69 (s, 2H)
IR (KBr) ν max: 1606, 1498, 1220 m$^{-1}$
Mass, m/e: 422 (M$^+$), 127 (base)

Example 48

5-(3,5-Difluorophenylacetylamino)-3-(4-fluorophenyl)-1-methyl-4-(4-pyridyl)pyrazole Melting point: 208.5–210.2° C.
$^1$H-NMR (CDCl$_3$) δ: 8.44 (dd, J=1.4, 4.5 Hz, 211), 7.42–6.70 (m, 10H), 3.77 (s, 3H), 3.72 (s, 2H)
IR (KBr) ν max: 1624, 1600, 1514, 1450, 1120 m$^{-1}$
Mass, m/e: 422 (M$^+$), 268 (base)

Example 49

5-(2,3-Difluorophenylacetylamno)-3-(4-fluorophenyl)-1-methyl-4-(4-pyridyl)pyrazole Melting point: 181.3–182.5° C. (diethyl ether)
$^1$H-NMR (CDCl$_3$) δ: 8.43 (dd, J=1.5, 4.4 Hz, 2H), 7.42–6.87 (m, 10H), 3.78 (s, 5H)
IR (KBr) ν max: 1678, 1606, 1494, 1220 m$^{-1}$
Mass, m/e: 422 (M$^+$), 127 (base)

Example 50

5-(3,5-Dimethylphenylacetylamino)-3-(4-fluorophenyl)-1-methyl-4-(4-pyridyl)pyrazole Melting point: 211.2–212.4° C.
$^1$H-NMR (CDCl$_3$) δ: 8.43 (dd, J=1.5, 4.6 Hz, 2H), 7.41–7.22 (m, 2H), 7.08–6.87 (m, 81), 3.77 (s, 311), 3.67 (s, 2H) 2.29 (s, 6H)
IR (KBr) ν max: 1670, 1606, 1522 cm$^{-1}$
Mass, m/e: 414 (M$^+$), 268 (base)

Example 51

5-(2,5-Dimethylphenylacetylanino)-3-(4-fluorophenyl)-1-methyl-4-(4-pyridyl)pyrazole Melting point: 179.9–185.1° C.
$^1$H-NMR (CDCl$_3$) δ: 8.46 (dd, J=1.6, 4.5 Hz, 2H), 7.40–7.22 (m, 2H), 7.09–6.78 (m, 8H), 3.78 (s, 3H), 3.70 (s, 2H), 2.31 (s, 3H), 2.15 (s, 3H)
IR (KBr) ν max: 3236, 1672, 1606, 1504 cm$^{-1}$
Mass, m/e: 414 (M$^+$), 268 (base)

Example 52

5-(2,4-Dimethoxyphenylacetylamino)-3-(4-fluorophenyl)-1-methyl-4-(4-pyridyl)pyrazole Melting point: 179.3–182.2° C.
$^1$H-NMR (CDCl$_3$) δ: 8.39 (dd, J=1.7, 4.5 Hz, 2H), 7.41–6.84 (m, 8H), 6.58–6.44 (m, 2H), 3.84 (s, 3H), 3.76 (s, 2H), 3.67 (s, 6H)
IR (KBr) ν max: 1674, 1604, 1512, 1450, 1208, 1156 cm$^{-1}$
Mass, m/e: 446 (M$^+$), 151 (base)

Example 53

5-(2,3-Dimethoxyphenylacetylamino)-3-(4-fluorophenyl)-1-methyl-4-(4-pyridyl)pyrazole Melting point: 185.4–193.4° C.
$^1$H-NMR (CDCl$_3$) δ: 8.33 (dd, J=1.7, 4.5 Hz, 2EI), 7.85 (br, 1H) 7.41–6.83 (m, 9H), 3.88 (s, 6H), 3.72 (s, 5H)
IR (KBr) ν max: 1603, 1477, 1225 cm$^{-1}$
Mass, m/e: 446 (M$^+$), 91 (base)

Example 54

3-(4-Fluorophenyl)-1-methyl-4-(4-pyridyl)-5-(3,4,5-trimethoxyphenylacetylamino)pyrazole Melting point: 178.1–180.4° C.
$^1$H-NMR (CDCl$_3$) δ: 8.45 (dd, J=1.5, 4.6 Hz, 2H), 7.41–7.26 (m, 2H), 7.19–6.84 (m, 5H), 6.45 (s, 2H), 3.85 (s, 3H), 3.79 (s, 9H), 3.68 (s, 2H)
IR (KBr) ν max: 1672, 1592, 1507, 1462, 1237, 1125 cm$^{-1}$
Mass, m/e: 476 (M$^+$), 181 (base)

Example 55

3-(4-Fluorophenyl)-1-methyl-5-(2,3,4,5,6-pentafluorophenylacetylamino)-4-(4-pyridyl)pyrazole Melting point: Amorphous
$^1$H-NMR (CDCl$_3$) δ: 8.45 (dd, J=1.1, 4.8 Hz, 2H), 7.89 (s, 1H), 7.5–6.7 (m, 61H), 3.85 (s, 2H), 3.82 (s, 3H)
IR (KBr) ν max: 1686, 1608, 1506, 1010, 840 cm$^{-1}$
Mass, m/e: 476 (M$^+$), 268 (base)

Example 56

5-(2-Chlorophenylacetylamino)-3-(4-fluorophenyl)-1-methyl-4-(4-pyridyl)pyrazole

Melting point: 215.9–217.8° C. (n-hexane-ethyl acetate)
$^1$H-NMR (DMSO-d$_6$) δ: 8.48 (dd, J=1.5, 4.6 Hz, 2H), 7.53–6.97 (m, 10H), 3.85 (s, 2H), 3.72 (s, 3H)
IR (KBr) ν max: 1680, 1604, 1520, 1222 cm$^{-1}$
Mass, m/e: 420 (M$^+$), 125 (base)

Example 57

5-(2-Bromophenylacetylamino)-3-(4-fluorophenyl)-1-methyl-4-(4-pyridyl)pyrazole

Melting point: 223.8–227.6° C.
$^1$H-NMR (CDCl$_3$) δ: 8.41 (dd, J=1.6, 4.5 Hz, 2H), 7.96 (br, 1H), 7.66–6.85 (m, 11H), 3.88 (s, 2H), 3.80 (s, 3H)
IR KBr) ν max: 1692, 1604, 1224 cm$^{-1}$
Mass, m/e: 464 (M$^+$), 268 (base)

Example 58

5-(3-Bromophenylacetylamino)-3-(4-fluorophenyl)-1-methyl-4-(4-pyridyl)pyrazole

Melting point: 78.5–80.2° C.

$^1$H-NMR (CDCl$_3$) δ: 8.45 (d, J=5.9 Hz, 2H), 7.47–6.89 (m, 10H), 3.76 (s, 3H), 3.71 (s, 2H)

IR (KBr) ν max: 3244, 3064, 1682, 1604, 1570, 1508, 1476, 1408, 1224, 840 cm$^{-1}$ Mass, m/e: 466 (M$^+$+2), 464 (M$^+$), 268 (base)

Example 59

5-(4-Bromophenylacetylamino)-3-(4-fluorophenyl)-1-methyl-4-(4-pyridyl)pyrazole

Melting point: 199.8–202.1° C.

$^1$H-NMR (CDCl$_3$) δ: 8.45 (d, J=6.2 Hz, 2H), 7.59–6.88 (m, 10H), 3.75 (s, 3H), 3.69 (s, 2H)

IR (KBr) ν max: 3228, 1664, 1602, 1568, 1514, 1488, 1448, 1220, 844 cm$^{-1}$

Mass, m/e: 466 (M$^+$+2), 464 (M$^+$), 268 (base)

Example 60

3-(4-Fluorophenyl)-5-(2-fluorophenylacetylamino)-1-methyl-4-(4-pyridyl)pyrazole

Melting point: 196.8–198.1° C. (n-hexane-ethyl acetate)

$^1$H-NMR (CDCl$_3$) δ: 8.42 (dd, J=1.5, 4.4 Hz, 21), 7.53–6.80 (m, 10H), 3.77 (s, 3H), 3.77 (s, 2H)

IR (KBr) ν max: 1678, 1606, 1516, 1222 cm$^{-1}$

Mass, m/e: 404 (M$^+$), 109 (base)

Example 61

3-(4-Fluorophenyl)-5-(3-fluorophenylacetylamino)-1-methyl-4-(4-pyridyl)pyrazole

Melting point: 196.9–199.1° C.

$^1$H-NMR (CDCl$_3$) δ: 8.43 (dd, J=1.5, 4.4 Hz, 2H), 7.44–6.87 (m, 11H), 3.76 (s, 3H), 3.74 (s, 2H)

IR (KBr) ν max: 1671, 1604, 1522, 1488, 1448, 1222 cm$^{-1}$

Mass, m/e: 404 (M$^+$), 268 (base)

Example 62

3-(4-Fluorophenyl)-5-(4-fluorophenylacetylamino)-1-methyl-4-(4-pyridyl)pyrazole

Melting point: 217.3–219.7° C. (n-hexane-ethyl acetate)

$^1$H-NMR (CDCl$_3$) δ: 8.45 (dd, J=1.8, 4.6 Hz, 2H), 7.45–6.65 (m, 10H), 3.75 (s, 3H), 3.72 (s, 2H)

IR (KBr) ν max: 1668, 1602, 1512, 1222 cm$^{-1}$

Mass, m/e: 404 (M$^+$), 109 (base)

Example 63

3-(4-Fluorophenyl)-5-(3-methoxyphenylacetylamino)-1-methyl-4-(4-pyridyl)pyrazole Melting point: 135.0–141.2° C.

$^1$H-NMR (CDCl$_3$) δ: 8.43 (dd, J=1.5, 4.6 Hz, 2H), 7.43–7.22 (m, 2H), 7.06–6.79 (m, 9H), 3.79 (s, 3H), 3.76 (s, 3H), 3.72 (s, 2H)

IR (KBr) ν max: 1604, 1491, 1448, 1221, 1157 cm$^{-1}$

Mass, m/e: 416 (M$^+$), 121 (base)

Example 64

3-(4-Fluorophenyl)-5-(4-methoxyphenylacetylamino)-1-methyl-4-(4-pyridyl)pyrazole Melting point: 172.3–176. 1° C. (n-hexane-ethyl acetate)

$^1$H-NMR (CDCl$_3$) δ: 8.46 (dd, J=1.5, 4.6 Hz, 2H), 7.46–6.65 (m, 10H), 3.82 (s, 3H), 3.76 (s, 3H), 3.68 (s, 2H)

IR (KBr) ν max: 1660, 1606, 1510, 1250 cm$^{-1}$

Mass, m/e: 416 (M$^+$), 121 (base)

Example 65

3-(4-Fluorophenyl)-1-methyl-5-(2-nitrophenylacetylamino)-4-(4-pyridyl)pyrazole

Melting point: 240.9–242.4° C.

$^1$H-NMR (CDCl$_3$) δ: 8.47–8.40 (m, 2H), 8.14–8.04 (m, 2H), 7.68–6.83 (m, 9H), 4.01 (s, 2H), 3.82 (s, 3H)

IR (KBr) ν max: 1694, 1604, 1575, 1522, 1342, 1227 cm$^{-1}$

Mass, m/e: 431 (M$^+$), 268 (base)

Example 66

3-(4-Fluorophenyl)- l-methyl-5-(3-nitrophenylacetylamino)-4-(4-pyridyl)pyrazole

Melting point: 220.2–230.2° C.

$^1$H-NMR (CDCl$_3$) δ: 8.47–8.11 (m, 4H), 7.70–6.87 (m, 9H), 3.86 (s, 2H1), 3.78 (s, 3H)

IR (KBr) ν max: 1698, 1687, 1630, 1604, 1562, 1526, 1484, 1477, 1450, 1354, 1225, 841 cm$^{-1}$ Mass, m/e: 431 (M$^+$), 268 (base)

Example 67

3-(4-Fluorophenyl)-1-methyl-5-(2-methylphenylacetylamino)-4-(4-pyridyl)pyrazole

Melting point: 197.6–200.5° C. (n-hexane-ethyl acetate)

$^1$H-NMR (CDCl$_3$) δ: 8.45 (dd, J=1.5, 4.6 Hz, 2H), 7.45–6.70 (m, 10H), 3.78 (s, 3H), 3.75 (s, 2H), 2.20 (s, 3H)

IR (KBr) ν max: 1670, 1606, 1506, 1222cm$^{-1}$

Mass, m/e, 400 (M$^+$), 105 (base)

Example 68

3-(4-Fluorophenyl)-1-methyl-4-(4-pyridyl)-5-(2-trifluoromethylphenylacetylamino)pyrazole Melting point: 242.7–244.5° C. (n-hexane-ethyl acetate)

$^1$H-NMR (CDCl$_3$) δ: 8.46 (dd, J=1.5, 4.6 Hz, 2H), 7.80–6.65 (m, 11H), 3.92 (bs, 2H), 3.77 (s, 3H)

IR (KBr) ν max: 1696, 1608, 1316 cm$^{-1}$

Mass, m/e: 454 (M$^+$), 159 (base)

Example 69

3-(4-Fluorophenyl)-5-(2-methoxyphenylacetylamino)-1-methyl-4-(4-pyridyl)pyrazole Melting point: 206.8–209.2° C.

$^1$H-NMR (CDCl$_3$) δ: 8.35 (dd, J=1.5 Hz, 4.5 Hz, 2H), 7.46–6.80 (m, 10H), 3.76 (s, 3H), 3.74 (s, 2H), 3.68 (s, 3H)

IR (KBr) ν max: 3224, 1674, 1604, 1498, 1248 cm$^{-1}$

Mass, m/e: 416 (M$^+$), 91 (base)

Example 70

5-(4-Benzyloxyphenylacetylamino)-3-(4-fluorophenyl)-1-methyl-4-(4-pyridyl)pyrazole Melting point: 147.8–150.1° C.
$^1$H-NMR (CDCl$_3$) δ: 8.39 (dd, J=1.5, 4.5 Hz, 2H), 7.47–6.85 (m, 15H), 5.09 (s, 2H), 3.73 (s, 3H), 3.65 (s, 3H)
IR (KBr) ν max: 3216, 1660, 1606, 1510, 1240, 840 cm$^{-1}$
Mass, m/e: 492 (M$^+$), 91 (base)

Example 71

3-(4-Fluorophenyl)-1-methyl-5-(4-methylthiophenylacetyl-amino)-4-(4-pyridyl)pyrazole Melting point: 182.5–184.7° C.
$^1$H-NMR (CDCl$_3$) δ: 8.44 (dd, J=1.5, 4.5 Hz, 2H), 7.41–6.88 (m, 10H), 3.75 (s, 3H), 3.70 (s, 2H), 2.50 (s, 3H)
IR (KBr) ν max: 3212, 1658, 1604, 1518, 1448, 1228, 836 cm$^{-1}$
Mass, m/e: 432 (M$^+$, base)

Example 72

3-(4-Fluorophenyl)-1-methyl-4-(4-pyridyl)-5-(3-trifluoromethylphenylacetylamino)pyrazole Melting point: 193.4–195.8° C.
$^1$H-NMR (CDCl$_3$) δ: 8.39 (d, J=5.9 Hz, 2H), 7.62–6.86 (m, 10H), 3.80 (s, 2H), 3.75 (s, 3H)
IR (KBr) ν max: 3236, 2952, 1678, 1608, 1568, 1506, 1450, 1334, 1222, 1164, 1126, 840 cm$^{-1}$
Mass, m/e: 454 (M$^+$), 268 (base)

Example 73

3-(4-Fluorophenyl)-1-methyl-5-(2-phenylpropionylamino)-4-(4-pyridyl)pyrazole

Melting point: 210.0–214.9° C. (n-hexane-ethyl acetate)
$^1$H-NMR (CDCl$_3$) δ: 8.37 (dd, J=1.5, 4.6 Hz, 2H), 7.50–6.65 (m, 11H), 3.90–3.55 (m, 1H) 3.72 (s, 3H), 1.60 (d, J=7.0 Hz, 3H)
IR (KBr) ν max: 1672, 1606, 1508, 1222 cm$^{-1}$
Mass, m/e: 400 (M$^+$), 105 (base)

Example 74

3-(4-Fluorophenyl)-5-(α-fluorophenylacetylamino)-1-methyl-4-(4-pyridyl)pyrazole

Melting point: 92.1–96.1° C. (n-hexane-ethyl acetate)
$^1$H-NMR (CDCl$_3$) δ: 8.43 (dd, J=1.5, 4.4 Hz, 2H), 7.93 (m, 1H), 7.50–6.90 (m, 11H), 5.97 (d, J=48.1 Hz, 1H), 3.79 (s, 3H)
IR (KBr) ν max: 1698, 1606, 1510, 1222 cm$^{-1}$
Mass, m/e: 404 (M$^+$), 109 (base)

Example 75

A mixture of 5-[(2-buten-1-oyl)amino]-3-(4-fluorophenyl)-1-methyl-4-(4-pyridyl)pyrazole and 5-[(3-buten-1-oyl)amino]-3-(4-fluorophenyl)-1-methyl-4-(4-pyridyl)pyrazole Melting point: Amorphous
$^1$H-NMR (CDCl$_3$) δ: 8.6–8.3 (m, 2H), 7.5–6.8 (m, 6H), 6.2–5.8 (m, 1H), 5.5–5.1 (m, 1H), 3.82 (s, 3H), 3.21 (d, J=7.0 Hz, 1.2H), 1.94 (dd, J=1.5, 7.0 Hz, 1.2H)
IR (KBr) ν max: 1680, 1606, 1222, 840 cm$^{-1}$
Mass, m/e: 336 (M$^+$), 268 (base)

Example 76

3-(4-Fluorophenyl)-1-methyl-4-(4-pyridyl)-5-(2-pyridylacetylamino)pyrazole

Melting point: 148.9–149.4° C. (n-hexane-ethyl acetate)
$^1$H-NMR (CDCl$_3$) δ: 10.04 (bs, 1H), 8.50–8.20 (m, 3H), 7.78 (dd, J=1.8, 7.9 Hz, 1H), 7.50–6.80 (m, 8H), 3.90 (s, 2H), 3.81 (s, 3H)
IR (KBr) ν max: 1670, 1604, 1222 cm$^{-1}$
Mass, m/e: 387 (M$^+$), 93 (base)

Example 77

3-(4-Fluorophenyl)-1-methyl-4-(4-pyridyl)-5-(3-pyridylacetylamino)pyrazole

Melting point: 220.0–220.9° C. (n-hexane-ethyl acetate)
$^1$H-NMR (CDCl$_3$) δ: 8.60–8.15 (m, 4H), 7.95–7.53 (m, 2H), 7.46–6.75 (m, 6H), 3.78 (s, 3H), 3.69 (s, 2H)
IR (KBr) ν max: 1700, 1604, 1220 cm$^{-1}$
Mass, m/e: 387 (M$^+$), 92 (base)

Example 78

3-(4-Fluorophenyl)-1-methyl-4-(4-pyridyl)-5-(4-pyridylacetylamino)pyrazole

Melting point: 141.3–143.4° C. (n-hexane-ethyl acetate)
$^1$H-NMR (CDCl$_3$) δ: 8.57 (d, J=5.9 Hz, 2H), 8.40 (d, J=5.9 Hz, 2H), 7.61 (bs, 1H), 7.47–6.70 (m, 8H), 3.76 (s, 3H), 3.76 (s, 2H)
IR (KBr) ν max: 1668, 1604, 1516 cm$^{-1}$
Mass, m/e: 387 (M$^+$), 92 (base)

Example 79

3-(4-Fluorophenyl)-1-methyl-5-(1-methylpyrrol-2-ylacetylamino)-4-(4-pyridyl)pyrazole Melting point: 165.1–168.1° C. (n-hexane-ethyl acetate)
$^1$H-NMR (CDC4) δ: 8.49 (dd, J=1.5, 4.4 Hz, 2H), 7.50–6.80 (m, 7H), 6.64 (dd, J=2.2, 2.4 Hz, 1H), 6.13 (d, J=2.2 Hz, 2H), 3.79 (s, 3H), 3.70 (s, 2H), 3.33 (s, 3H)
IR (KBr) ν max: 1672, 1606, 1506, 1222 cm.$^{-1}$
Mass, m/e: 389 (M$^+$), 94 (base)

Example 80

3-(4-Fluorophenyl)-1-methyl-4-(4-pyridyl)-5-(3-thienylacetylamino)pyrazole

Melting point: 151.9–154.6° C. (n-hexane-ethyl acetate)
$^1$H-NMR (CDCl$_3$) δ: 8.46 (dd, J=1.5, 4.4 Hz, 2H), 7.50–6.83 (m, 9H), 3.77 (s, 3H), 3.77 (s, 2H)
IR (KBr) ν max: 1668, 1606, 1506, 1222 cm$^{-1}$
Mass, m/e: 392 (M$^+$), 97 (base)

Example 81

3-(4-Fluorophenyl)-1-methyl-5-(1-pyrazolylacetyiniino)-4-(4-pyridyl)pyrazole

Melting point: 144.7–146.3° C. (n-hexane-ethyl acetate)
$^1$H-NMR (CDCl$_3$) δ: 8.55 (bs, 1H), 8.44 (dd, J=1.5, 4.4 Hz, 2H), 7.64 (d, J=1.8 Hz, 1H), 7.55–6.83 (m, 7H), 6.40 (dd, J=2.0, 2.2 Hz, 1H) 4.95 (s, 2H), 3.79 (s, 3H)
IR (KBr) ν max: 1690, 1606, 1518, 1222 cm$^{-1}$
Mass, m/e: 376 (M$^+$), 295 (base)

Example 82

3-(4-Fluorophenyl)-5-(indol-3-ylacetylamino)-1-methyl-4-(4-pyridyl)pyrazole

Melting point: 66.9–68.8° C.
$^1$H-NMR (CDCl$_3$) δ: 8.65–6.75 (m, 13H), 3.86 (d, J=4.0 Hz, 2H), 3.75 (s, 3H)
IR (KBr) ν max: 3418, 1694, 1607, 1439, 1221 cm$^{-1}$

Example 83

Synthesis of 5-(2-chloro-6-fluoro-3-nitrophenylacetylamino)-3-(4-fluorophenyl)-1-methyl-4-(4-pyridyl)pyrazole (a) Synthesis of 2-chloro-6-fluoro-3-nitrophenylacetic Acid 1.89 g of 2-chloro-6-fluoro-phenylacetic acid was suspended in 20 ml of concentrated nitric acid. After the addition of 10 ml of concentrated sulfuric acid, the resulting mixture was heated under reflux for 3.5 hours. After the reaction mixture was poured into ice water, the resulting precipitate was collected by filtration, washed with a small amount of purified water, and then dried. Thus, 1.83 g (78% yield) of the title compound was obtained as a white powder.

Melting point: 145.0° C.
$^1$H-NMR (CDCl$_3$) δ: 7.88 (dd, J=9.2, 5.3 Hz, 1H), 7.17 (dd, J=9.1, 7.9 Hz, 1H), 3.98 (d, J=2.2 Hz, 2H)
IR (KBr) ν max: 3500–2500, 1698, 1536w 1342 cm$^{-1}$ (b) Synthesis of 5-(2-chloro-6-fluoro-3-nitrophenylacetylamino)-3-(4-fluorophenyl)-1-methyl-4-(4-pyridyl)pyrazole The title compound was obtained by effecting reaction in the same manner as in Example 35, except that the 2-chloro-6-fluoro-3-nitrophenylacetic acid obtained in the above step (a) was used in place of 2,5-difluorophenylacetic acid.

Melting point: 129.2–130.6° C.
$^1$H-NMR (CDCl$_3$) δ: 8.47 (d, J=4.8 Hz, 2H), 7.89 (m, 1H)>7.36–6.97 (m, 7H), 4.07 (d, J=2.0 Hz, 2H), 3.83 (s, 3H)
IR (KBr) ν max: 1684, 1606, 1532, 1352 cm$^{-1}$
Mass, m/e: 483 (M$^+$), 268 (base)

Example 84

Synthesis of 3-(N'-carbobenzoxy-L-alanylamino)-5-(4-fluorophenyl)-4-(4-pyridyl)pyrazole Under a stream of argon gas, 421 mg of Z-L-alanine and 306 mg of carbonyldiimidazole (CDI) were dissolved in 10 ml of tetrahydrofuran, followed by stirring at room temperature for 10 minutes. Then, 150 mg of 5-amino-3-(4-fluorophenyl)-4-(4-pyridyl)pyrazole and 287 mg of 1,8-diazabicyclo[5.4.2]undec-7-ene (DBU) were added thereto, followed by stirring at room temperature for 4 hours. After the reaction mixture was concentrated under reduced pressure, the resulting residue was purified by column chromatography using 20 g of silica gel [with an elution solvent comprising chloroform-methanol (50:1)]. Thus, 88 mg (32% yield) of the title compound was obtained as a white powder.

Melting point: 190.0–191.3° C.
$^1$H-NMR (CDCl$_3$) δ: 8, 48 (dd, J=1.5 Hz, 2H), 7.41–6.99 (m, 11H), 5.09 (s, 2H), 4.04 (m, 1H), 1.45 (d, J=7.0 Hz, 3H)
IR (KBr) ν max: 3500–2500, 1682, 1608 cm$^{-1}$
Mass, m/e: 459 (M$^+$), 91 (base)

The compounds of the following Examples 85–89 were synthesized in the same manner as in Example 35.

Example 85

3-(N'-carbobenzoxy-L-valylamino)-5-(4-fluorophenyl)-4-(4-pyridyl)pyrazole

Melting point: 231.1° C.
$^1$H-NMR (CDCl$_3$) δ: 8.47 (dd, J=1.5, 4.4 Hz, 2H), 7.40–7.21, 7.03–6.91 (m, 9H), 7.14 (dd, J=1.5, 4.4 Hz, 2H), 6.02 (br d, J=9.2 Hz, 1H), 5.10 (s, 2H), 4.10 (m, 1H), 2.18 (m, 1H), 0.98 (dd, J=3.7, 6.8 Hz, 6H)
IR (KBr) ν max: 3500–2500, 1688, 1610, 1512 cm$^{-1}$
Mass, m/e: 487 (M$^+$), 91 (base)

Example 86

3-(N'-Carbo-t-butoxy-L-alanylamino)-5-(4-fluorophenyl)-4-(4-pyridyl)pyrazole

Melting point: 223.0–224.7° C.
$^1$H-NMR (CDCl$_3$) δ: 8.53 (dd, J=1.5, 4.4 Hz, 2H), 7.42–7.27, 7.08–6.92 (m, 4H), 7.18 (dd, J=1.5, 4.4 Hz, 2H), 5.40 (br d, 1H), 4.30 (m, 1H), 1.44 (d, J=6.8 Hz, 3H), 1.38 (s, 9H)
IR (KBr) ν max: 3600–2700, 3280, 1680, 1608, 1516 cm$^{-1}$
Mass, m/e: 425 (M$^+$), 281 (base)

Example 87

3-(N'-Carbo-t-butoxy-L-valylamino)-5-(4-fluorophenyl)-4-(4-pyridyl)pyrazole

Melting point: 217.1–217.6° C.
$^1$H-NMR (CDCl$_3$) δ: 8.54 (dd, J=1.5, 4.4 Hz, 2H), 7.42–7.24, 7.11–6.92 (m, 4H), 7.18 (dd, J=1.5, 4.4 Hz), 5.36 (br d, J=8.8 Hz, 1H), 4.00 (m, 1H), 1.42 (s, 9H), 0.99 (dd, J=3.7, 6.6 Hz, 6H)
IR (KBr) ν max: 3600–2700, 3208, 2980, 1664, 1608, 1512 cm$^{-1}$
Mass, m/e: 453 (M$^+$), 254 (base)

Example 88

3-(N'-Carbo-t-butoxy-L-prolylamino)-5-(4-fluorophenyl)-4-(4-pyridyl)pyrazole

Melting point: 124.6–125.7° C.
$^1$H-NMR (CDCl$_3$) δ: 10.43 (bs, 1H), 8.60 (dd, J=1.5, 4.4 Hz, 2H), 7.46–7.22, 7.08–6.88 (m, 4H), 7.16 (dd, J=1.5, 4.4 Hz, 2H), 4.51 (br d, J=5.9 Hz, 1H), 3.41 (m, 2H), 2.04 (m, 4H), 1.34 (s, 9H)
IR (KBr) ν max: 3600–2400, 1652, 1604, 1506 cm$^{-1}$
Mass, m/e: 451 (M$^+$), 281 (base)

Example 89

3-(N'-Carbo-t-butoxy-N'-methyl-L-Phenylalanylamino)-5-(4-fluorophenyl)-4-(4-pyridyl)pyrazole Melting point: 232.4–233.1° C.
$^1$H-NMR (CDCl$_3$) δ: 8.52 (dd, J=1.5, 4.6 Hz, 2H), 7.42–7.26, 7.01–6.91 (m, 9H), 7.08 (dd, J=1.8, 4.6 Hz, 2H), 4.89 (m, 1H), 3.23 (m, 2H), 2.77 (s, 3H), 1.33 (s, 9H)
IR (KBr) ν max: 3336, 2976, 1672, 1590 cm$^{-1}$
Mass, m/e: 515 (M$^+$), 57 (base)

Example 90

Synthesis of 3-(L-alanylamino)-5-(4-fluorophenyl)-4-(4-pyridyl)pyrazole hydrochloride 80 mg of 5-(4-fluorophenyl)-3-(N'-carbo-t-butoxy-L-alanylamino)-4-(4-pyridyl)pyrazole was dissolved in 2 ml of ethyl acetate. Then, 5 ml of a 2.9 mol/L solution of HCl in ethyl acetate was added thereto, followed by stirring at room temperature overnight. After the reaction mixture was concentrated under reduced pressure, the resulting residue was suspended in ethyl acetate. The precipitated powder was collected by filtration to obtain 60 mg (73% yield) of the title compound as a white powder.

Melting point: 210.2–211.5° C.
$^1$H-NMR (CD$_3$OD) δ: 8.73 (br d, J=6.2 Hz, 2H), 7.86 (br d, J=4.8 Hz, 2H), 7.56–7.13 (m, 4H), 4.14 (q, J=7.0 Hz, 1H), 1.69 (d, J=7.2 Hz, 3H)
IR (KBr) ν max: 3500–2500, 1700, 1632, 1514 cm$^{-1}$
Mass, m/e: 325 (M$^+$), 254 (base)

The compound of the following Example 91 was synthesized in substantially the same manner as in Example 90.

Example 91

5-(4-Fluorophenyl)-4-(4-pyridyl)-3-(L-valylamino) pyrazole hydrochloride

Melting point: 205.3–206.4° C.
$^1$H-NMR (CD$_3$OD) δ: 8.72 (br d, J=3.7 Hz, 2H), 7.90 (br d, J=3.7 Hz, 2H), 7.55–7.13 (m, 4H), 4.06 (m, 1H), 2.37 (m, 1H), 1.26–1.05 (m, 6H)
IR (KBr) ν max: 3500–2500, 1692, 1632, 1500 cm$^{-1}$
Mass, m/e: 353 (M$^+$), 72 (base)

Example 92

Synthesis of 5-(4-fluorophenyl)-3-(2-nitrophenylacetylamino)-4-(4-pyridyl)pyrazole Under a stream of argon gas, 543 mg of 2-nitrophenylacetic acid and 486 mg of carbonyldiimidazole were dissolved in 10 ml of tetrahydrofuran, followed by stirring at room temperature for 10 minutes. Then, 254 mg of 3-amino-5-(4-fluorophenyl)-4-(4-pyridyl)pyrazole and 457 mg of DBU were added thereto, followed by stirring at room temperature overnight. After the reaction mixture was concentrated under reduced pressure, the resulting residue was suspended in chloroform, washed with a saturated aqueous solution of sodium bicarbonate and a saturated aqueous solution of sodium chloride, dried over anhydrous magnesium sulfate, and then concentrated. The resulting residue was purified by column chromatography using 40 g of silica gel [with an elution solvent comprising chloroform-methanol (100:1)]. Thus, 70 mg (14% yield) of the title compound was obtained as a white powder.

Melting point: 242.4–244.1° C.
$^1$H-NMR (CDCl$_3$) δ: 8, 47 (m, 2H), 8.05 (br d, J=8.1 Hz, 1H), 7.66–6.98 (m, 10H), 4.62 (s, 2H)
IR (KBr) ν max: 3500–2500, 1670, 1602cm$^{-1}$
Mass, m/e: 417 (M$^+$), 254 (base)

Example 93

Synthesis of 5-(4-fluorophenyl)-3-(2-aminophenylacetylamino)-4-(4-pyridyl)pyrazole 11 mg of 5-(4-fluorophenyl)-3-(2-nitrophenylacetylamino)-4-(4-pyridyl)pyrazole was dissolved in 5 ml of methanol. Then, 100 mg of cyclohexene and 20 mg of 5% palladium-carbon were added thereto, followed by heating under reflux for 1 hour. After the reaction mixture was filtered, the filtrate was concentrated under reduced pressure to obtain 8 mg (79% yield) of the title compound as a light-brown powder.

Melting point: 196.3–197.1° C.
$^1$H-NMR (CD$_3$OD) δ: 8, 35 (m, 2H), 7.59–6.84 (m, 10H), 4.60 (br s, 2H)
IR (KBr) ν max: 3500–2000, 1676, 1602 cm$^{-1}$
Mass, m/e: 387 (M$^+$), 254 (base)

The compound of the following Example 94 was synthesized in substantially the same manner as in Example 93.

Example 94

5-(3-Aminophenylacetylamino)-3-(4-fluorophenyl)-1-methyl-4-(4-pyridyl)pyrazole

Melting point: 110.6–119.0° C.
$^1$H-NMR (CDCl$_3$) δ: 8.45 (dd, J=1.6, 4.5 Hz, 2H), 7.60–6.46 (m, 11H), 3.76 (s, 3H), 3.63 (s, 2H), 1.63 (br, 2H)
IR (KBr) ν max: 1675, 1608, 1509, 1449, 1222 cm$^{-1}$
Mass, m/e: 401 (M$^+$), 106 (base)

Example 95

Synthesis of 5-(4-hydroxyphenylacetylamino)-3-(4-fluorophenyl)-1-methyl-4-(4-pyridyl)pyrazole Under a stream of argon gas, 0.11 g of 5-(4-benzyloxyphenylacetylamino)-3-(4-fluorophenyl)-1-methyl-4-(4-pyridyl)pyrazole, 22.9 mg of palladium hydroxide-carbon, and 8 ml of cyclohexene were added to 15 ml of ethanol followed by heating under reflux for 23 hours. After the reaction mixture was cooled to room temperature, the catalyst was filtered off and the solvent was distilled off under reduced pressure. The resulting residue was purified by column chromatography using 30 g of silica gel [with an elution solvent comprising chloroform-methanol (100:0–40:1)]. Thus, 61.3 mg (69% yield) of the title compound was obtained as white crystals.

Melting point: 127.1–128.6° C.
$^1$H-NMR (CD$_3$OD) δ: 8.29 (d, J=6.2 Hz, 2H), 7.84–6.68 (m, 10H), 3.73 (s, 3H), 3.58 (s, 2H)
IR (KBr) ν max: 3224, 1676, 1606, 1514, 1450, 1224, 840 cm$^{-1}$
Mass, m/e: 402 (M$^+$), 107 (base)

Example 96

Synthesis of 5-amino-3-(4-fluorophenyl)-1-methyl-4-(4-pyridyl)pyrazole and 3-amino-5-(4-fluorophenyl)-1-methyl-4-(4-pyridyl)pyrazole While a dimethylformamide suspension containing 0.17 g of 60% sodium hydride was being cooled with ice, 10 ml of a dimethylformamide solution containing 1.00 g of 3-amino-5-(4-fluorophenyl)-4-(4-pyridyl)pyrazole was added dropwise thereto, followed by stirring at room temperature for 30 minutes. Then, 5 ml of a dimethylformamide solution containing 0.67 g of methyl iodide was added dropwise thereto, followed by stirring at room temperature for 3 hours. After the dimethylformamide was distilled off under reduced pressure, the resulting residue was extracted with chloroform. The organic layer was washed with water and dried over anhydrous magnesium sulfate. After the solvent was distilled off under reduced pressure, the resulting residue was purified by column chromatography using 250 g of silica gel [with an elution solvent comprising chloroform-methanol (20:1)]. Thus, 0.34 g (32% yield) of 3-amino-5-(4-fluorophenyl)-1-methyl-4-(4-pyridyl)pyrazole (light-brown crystals) was obtained as a first elution product, and 0.45 g (43% yield) of 5-amino-3-(4-fluorophenyl)-1-methyl-4-(4-pyridyl)pyrazole (light-brown crystals) as a second elution product.

First elution product

Melting point: 194.6–195.7° C.

$^1$H-NMR (CDCl$_3$) δ: 8.43 (dd, J=1.5, 4.4 Hz, 2H), 7.35–6.95 (m, 4H), 7.02 (dd, J=1.5, 4.4 Hz, 2H), 3.81 (bs, 2H), 3.61 (s, 3H)

IR (KBr) ν max: 3308, 1600, 1218

Mass, m/e: 268 (M$^+$, base)

Second elution product

Melting point: 155.2–157.9° C.

$^1$H-NMR (CDCl$_3$) δ: 8.53 (dd, J=1.5, 4.4 Hz, 2H), 7.50–6.83 (m, 4H), 7.08 (dd, J=1.5, 4.4 Hz, 2H), 3.77 (bs, 2H), 3.77 (s, 3H)

IR (KBr) ν max: 1598, 1212

Mass, m/e: 268 (M$^+$, base)

The compounds of the following Examples 97–103 were synthesized in substantially the same manner as in Example 96.

Example 97

1-Ethyl-3-(4-fluorophenyl)-5-phenylacetylamino-4-(4-pyridyl)pyrazole

Melting point: 219.0–221.2° C. (n-hexane-ethyl acetate)

$^1$H-NMR (CDCl$_3$) δ: 8.43 (dd, J=1.5, 4.6 Hz, 2H), 7.50–6.70 (m, 11H), 4.02 (q, J=7.5 Hz, 2H), 3.74 (s, 2H), 1.45 (t, J=7.5 Hz, 3H)

IR (KBr) ν max: 1680, 1604, 1528, 1218 cm$^{-1}$

Mass, m/e: 400 (M$^+$), 282 (base)

Example 98

5-(2-Chlorophenylacetylamino)-1-ethyl-3-(4-fluorophenyl)-4-(4-pyridyl)pyrazole

Melting point: 226.0–232.3° C. (n-hexane-ethyl acetate)

$^1$H-NMR (CDCl$_3$) δ: 8.43 (dd, J=1.5, 4.4 Hz, 2H), 7.55–6.70 (m, 10H), 4.06 (q, J=7.3 Hz, 2H), 3.87 (s, 2H), 1.46 (t, J=7.3 Hz, 3H)

IR (KBr) ν max: 1672, 1606, 1510, 1220 cm$^{-1}$

Mass, m/e: 434 (M$^+$), 282 (base)

Example 99

3-(4-Fluorophenyl)-5-phenylacetylamino-1-propyl-4-(4-pyridyl)pyrazole

Melting point: 176.5–178.5° C. (n-hexane-ethyl acetate)

$^1$H-NMR (CDCl$_3$) δ: 8.43 (dd, J=1.5, 4.6 Hz, 2H), 7.50–6.70 (m, 11H), 3.90 (t, J=7.5 Hz, 2H), 3.73 (s, 2H), 1.86 (m, 2H), 0.91 (t, J=7.5 Hz, 3H)

IR (KBr) ν max: 1668, 1606, 1524, 1220 cm$^{-1}$

Mass, m/e: 414 (M$^+$), 91 (base)

Example 100

1-Ethyl-3-(4-fluorophenyl)-4-(4-pyridyl)-5-(2-pyridylacetylamino)pyrazole

Melting point: 147.5–149.5° C. (n-hexane-ethyl acetate)

$^1$H-NMR (CDCl$_3$) δ: 9.89 (bs, 1H), 8.53–8.40 (m, 1H), 8.32 (dd, J=1.5, 4.4 Hz, 2H), 7.86–7.55 (m, 1H), 7.50–6.83 (m, 8H), 4.08 (q, J=7.3 Hz, 2H), 3.89 (s, 2H), 1.48 (t, J=7.3 Hz, 3H)

IR (KBr) ν max: 1668, 1606, 1512 cm$^{-1}$

Mass, m/e: 401 (M$^+$), 309 (base)

Example 101

1-Ethyl-3-(4-fluorophenyl)-5-(1-pyrazolylacetylamino)-4-(4-pyridyl)pyrazole

Melting point: 161.6–169.7° C. (n-hexane-ethyl acetate)

$^1$H-NMR (CDCl$_3$) δ: 8.44 (bs, 1H), 8.44 (dd, J=1.5, 4.6 Hz, 2H), 7.65 (d, J=1.8 Hz, 1H), 7.56–6.83 (m, 7H), 6.40 (dd, J=2.0, 2.2 Hz, 1H), 4.94 (s, 2H), 4.05 (q, J=7.3 Hz, 2H), 1.47 (t, J=7.3 Hz, 3H)

IR (KBr) ν max: 1690, 1606, 1522 cm$^{-1}$

Mass, m/e: 390 (M$^+$), 309 (base)

Example 102

1-(2-Dimethylaminoethyl)-3-(4-fluorophenyl)-5-(2-methoxyphenylacetylamino)-4-(4-pyridyl)pyrazole Melting point: Amorphous $^1$H-NMR (CDCl$_3$) δ: 8.36 (bd, J=4.4 Hz, 2H), 7.5–6.8 (m, 10H), 4.13 (t, d=5.9 Hz, 2H), 3.75 (s, 3H), 3.68 (s, 2H), 2.75 (t, J=5.9 Hz, 2H), 2.24 (s, 6H)

IR (KBr) ν max: 3220, 2948, 1668, 1606, 1224, 842 cm$^{-1}$

Mass, m/e: 403, 58 (base)

Example 103

1-(2-Benzyloxyethyl)-3-(4-fluorophenyl)-5-(2-methoxyphenylacetylamino)-4-(4-pyridyl)pyrazole Melting point: 142.9–144.2° C.

$^1$H-NMR (CDCl$_3$) δ: 8.39 (dd, J=1.5, 4.6 Hz, 2H), 7.65 (bs, 1H), 7.5–6.8 (m, 15H), 4.38 (s, 2H), 4.22 (t, J=5.3 Hz, 2H), 3.79 (t, J=5.3 Hz, 2H), 3.67 (s, 3H), 3.63 (s, 2H)

IR (KBr) ν max: 1684, 1604, 1248, 1224, 1104, 838 cm$^{-1}$

Mass, m/e: 536 (M$^+$), 91 (base)

Example 104

Synthesis of 3-(4-fluorophenyl)-1-(2-hydroxyethyl)-5-(2-methoxyphenylacetylamino)-4-(4-pyridyl)pyrazole The title compound was obtained by treating 1-(2-benzyloxyethyl)-3-(4-fluorophenyl)-5-(2-methoxyphenylacetylamino)-4-(4-pyridyl)pyrazole in substantially the same manner as in Example 95.

Melting point: 200.6–204.2° C. (ethanol-n-hexane)

$^1$H-NMR (CDCl$_3$) δ: 8.36 (dd, J=1.5, 4.4 Hz, 2H), 7.61 (s, 1H), 7.5–6.7 (m, 10H), 4.09 (m, 4H), 4.22 (t, J=5.3 Hz, 2H), 3.79 (t, J=5.3 Hz, 2H), 3.71 (s, 5H), 3.03 (bs, 1H)

IR (KBr) ν max: 3216, 1672, 1608, 1512, 1246 cm$^{-1}$

Mass, m/e: 446 (M$^+$), 91 (base)

The compounds of the following Examples 105 and 106 were synthesized in substantially the same manner as in Examples 103 and 104.

Example 105

3-(4-Fluorophenyl)-1-(2-hydroxyethyl)-5-phenylacetylamino-4-(4-pyridyl)pyrazole

Melting point: 180.3–183.6° C. (n-hexane-methylene chloride)

$^1$H-NMR (CDCl$_3$) δ: 8.44 (dd, J=1.3, 4.6 Hz, 2H), 7.5–6.8 (m, 11H), 4.23–3.90 (m, 4H), 3.71 (s, 2H)

IR (KBr) ν max: 3444, 1668, 1608, 1450, 1222, 840 cm$^{-1}$

Mass, m/e: 416 (M$^+$), 91 (base)

Example 106

5-(2-Chlorophenylacetylamino)-3-(4-fluorophenyl)-1-(2-hydroxyethyl)-4-(4-pyridyl)pyrazole Melting point: Amorphous
$^1$H-NMR (CDCl$_3$) δ: 8.43 (dd, J=1.5, 4.6 Hz, 2H), 7.5–6.8 (m, 10H), 4.3–3.9 (m, 4H), 3.84 (s, 2H)
IR (KBr) ν max: 3464, 1670, 1608, 1222 cm$^{-1}$
Mass, m/e: 450 (M$^+$), 254 (base)

Example 107

Synthesis of 5-(2-chlorophenylacetylamino)-3-(4-fluorophenyl)-1-phenyl-4-(4-pyridyl)pyrazole Step (c) of Example 34 was repeated by using phenylhydrazine in place of 1-methyl-t-butyl carbazate. The resulting 5-amino-3-(4-fluorophenyl)-1-phenyl-4-(4-pyridyl)pyrazole was reacted with 2-chlorophenylacetic acid in the same manner as in Example 35 to obtain the title compound.

Melting point: 265.2–268.0° C.
$^1$H-NMR (DMSO-d$_6$) δ: 10.25 (s, 1H), 8.55 (d, J=4.5 Hz, 2H), 7.67–7.10 (m, 15H), 3.69 (s, 2H)
IR (KBr) ν max: 3224, 1648, 1606, 1520, 1498, 836 cm$^{-1}$
Mass, m/e: 482 (M$^+$), 330 (base)

The compound of the following Example 108 was synthesized in substantially the same manner as in Example 107.

Example 108

3-(4-Flurophenyl)-5-(2-phenylpropionylamino)-1-phenyl-4-(4-pyridyl)pyrazole

Melting point: 240.4–242.5° C.
$^1$H-NMR (CDCl$_3$) δ: 8.45 (dd, J=1.5, 4.5 Hz, 2H), 7.50–6.88 (m, 16H), 6.71 (s, 1H), 3.62–3.44 (m, 1H), 1.46 (d, J=7.0 Hz, 3H)
IR (KBr) ν max: 3248, 1668, 1608, 1598, 1500, 1452, 1360, 1218, 844 cm$^{-1}$
Mass, m/e: 462 (M$^+$), 105 (base)

Example 109

Synthesis of 1-methyl-3-(3,4-methylenedioxyphenyl)-5-phenylacetylamino-4-(4-pyridyl)pyrazole Step (a) of Example 34 was repeated by using 2,5-dioxopyrroldinyl 3,4-methylenedioxybenzoate in place of 2,5-dioxopyrrolidinyl 4-fluorobenzoate. The resulting 3-(3,4-methylenedioxyphenyl)-3-oxo-2-(4-pyridyl)propionitrile was treated in the same manner as in step (c) of Example 34 to obtain 5-amino-1-methyl-3-(3,4-methylenedioxyphenyl)-4-(4-pyridyl)pyrazole. This compound was treated in the same manner as m Example 35 to obtain the title compound.

Melting point: 127.5–132.1° C. (n-hexane-ethyl acetate)
$^1$H-NMR (CDCl$_3$) δ: 8.45 (dd, J=2.8, 4.4 Hz, 2H), 7.4–6.6 (m, 8H), 5.93 (s, 2H), 3.74 (s, 2H), 3.74 (s, 3H)
IR (KBr) ν max: 1670, 1464, 1038, 1352 cm$^{-1}$
Mass, m/e: 413 (M$^+$), 293 (base), 91

The compounds of the following Examples 110–115 were synthesized in substantially the same manner as in Example 109.

Example 110

5-(3-Chloro-4-fluorophenylacetylamino)-1-methyl-3-(3,4-methylenedioxyphenyl)-4-(4-pyridyl)pyrazole Melting point: 206.9–208.7° C. (n-hexane-ethyl acetate)
$^1$H-NMR (CDCl$_3$) δ: 8.48 (dd, J=2.8, 4.4 Hz, 2H), 7.4–6.6 (m, 8H), 5.93 (s, 2H), 3.83 (s, 2H), 3.78 (s, 3H)
IR (KBr) ν max: 1669, 1494, 1040, 1352 cm$^{-1}$
Mass, m/e: 464 (M$^+$), 294 (base), 142

Example 111

3-(3,4-Dichlorophenyl)-1-methyl-5-phenylacetylamino-4-(4-pyridyl)pyrazole

Melting point: 198.4–199.1° C. (ethyl acetate)
$^1$H-NMR (CDCl$_3$) δ: 8.48 (dd, J=1.5, 4.4 Hz, 2H), 7.70–6.76 (m, 10H), 3.76 (s, 3H), 3.75 (s, 2H)
IR (KBr) ν max: 3400, 1700, 1604, 1248 cm$^{-1}$
Mass, m/e: 436 (M$^+$), 61 (base)

Example 112

3-(3-Chloro-4-fluorophenyl)-5-(2-chloro-4-fluorophenylacetylamino)-1-methyl-4-(4-pyridyl)pyrazole Melting point: 162.8–163.9° C. (ethyl acetate)
$^1$H-NMR (CDCl$_3$) δ: 8.47 (dd, J=1.7, 4.4 Hz, 2H), 7.62–6.82 (m, 8H), 3.80 (s, 3H), 3.80 (s, 2H)
IR (KBr) ν max: 3472, 1694, 1606, 1246 cm$^{-1}$
Mass, m/e: 472 (M$^+$), 143 (base)

Example 113

3-(3-Chloro-4-fluorophenyl)-1-methyl-5-phenylacetylamino-4-(4-pyridyl)pyrazole

Melting point: 194.2–194.7° C. (ethyl acetate)
$^1$H-NMR (CDCl$_3$) δ: 8.47 (dd, J=1.7, 4.4 Hz, 2H), 7.58–6.66 (m, 10H), 3.76 (s, 3H), 3.76 (s, 2H)
IR (KBr) ν max: 3448, 1688, 1606, 1236 cm$^{-1}$
Mass, m/e: 420 (M$^+$), 91 (base)

Example 114

3-(3-Chloro-4-fluorophenyl)-1-methyl-5-(2,3,4,5,6-pentafluorophenylacetylamino)4-(4-pyridyl)pyrazole Melting point: 194.7–196.0° C. (ethyl acetate)
$^1$H-NMR (CDCl$_3$) δ: 8.50 (dd, J=1.5, 4.6 Hz, 2H), 7.60–6.95 (m, 5H), 3.81 (s, 3H), 3.81 (s, 2H)
IR (KBr) ν max: 3456, 1706, 1606, 1238 cm$^{-1}$
Mass, m/e: 510 (M$^+$), 181 (base)

Example 115

5-(2-Chloro-4-fluorophenylacetylamino)-3-(3,4-dichlorophenyl)-1-methyl-4-(4-pyridyl)pyrazole Melting point: 279.3–280.1° C. (ethyl acetate)
$^1$H-NMR (CDCl$_3$) δ: 8.48 (dd, J=1.5, 4.4 Hz, 2H), 7.62–6.86 (m, 8H), 3.81 (s, 3H), 3.81 (s, 2H)
IR (KBr) ν max: 3480, 1692, 1606, 1244 cm$^{-1}$
Mass, m/e: 488 (M$^+$), 143 (base)

Example 116

Synthesis of 5-(4-fluorophenyl)-1-methyl-3-phenylacetylamino-4-(4-pyridyl)pyrazole 338 mg of 3-amino-5-(4-fluorophenyl)-1-methyl-4-(4-pyridyl)pyrazole was dissolved in 20 ml of a tetrahydrofuran, followed by the addition of 140 mg of triethylamine. Then, 5 ml of a tetrahydrofuran solution containing 214 mg of phenylacetyl chloride was added dropwise thereto, followed by stirring at room temperature overnight. After the addition of water, the reaction mixture was extracted with chloroform. After the organic layer was washed with water and dried over anhydrous magnesium sulfate, the solvent was distilled off under reduced pressure. The resulting residue was purified by column chromatography using 80 g of silica gel [with an elution solvent comprising chloroform-methanol (40:1)]. Thus, 310 mg (64% yield) of the title compound was obtained as pale-yellow crystals.

Melting point: 157.6–160.1° C. (isopropyl ether)
$^1$H-NMR (CDCl$_3$) δ: 8.33 (dd, J=1.6, 4.5 Hz, 2H), 7.47–6.90 (m, 10H), 6.77 (dd, J=1.6, 4.5 Hz, 2H), 3.73 (s, 21), 3.73 (s, 3H)
IR (KBr) ν max: 1602, 1220
Mass, m/e: 386 (M$^+$), 268 (base)

The compounds of the following Examples 117 and 118 were synthesized in substantially the same manner as in Example 116.

Example 117

3-(4-Fluorophenyl)-1-methyl-5-phenylacetylamino-4-(4-pyridyl)pyrazole

Melting point: 164.9–166.5° C. (n-hexane-ethyl acetate)
$^1$H-NMR (CDCl$_3$) δ: 8.40 (d, J=5.9 Hz, 21), 7.50–6.66 (m, 12H), 3.74 (s, 2H), 3.74 (s, 3H)
IR (KBr) ν max: 1602, 1220 cm$^{-1}$
Mass, m/e: 386 (M$^+$), 91 (base)

Example 118

3-(2-Chlorophenylacetylamino)-5-(4-fluorophenyl)-1-methyl-4-(4-pyridyl)pyrazole

Melting point: 193.8–195.3° C.
$^1$H-NMR (CDCl$_3$) δ: 8.32 (dd, J=1.5, 4.5 Hz, 2H), 7.48–6.99 (m, 8H), 6.84 (dd, J=1.5, 4.5 Hz, 2H), 3.86 (s, 2H1), 3.73 (s, 3H)
IR (KBr) ν max: 3236, 1662, 1602, 1512 cm$^{-1}$
Mass, m/e: 420 (M$^+$), 125 (base)

Example 119

Synthesis of 5-(4-fluorophenyl)-1-methyl-3-(N-methyl-N-phenylacetylamino)-4-(4-pyridyl)pyrazole While 2 1m of a dimethylformamide suspension containing 20 mg of 60% sodium hydride was being cooled with ice, 3 ml of a dimethylformamide solution containing 180 mg of 5-(4-fluorophenyl)-1-methyl-3-phenylacetylamino-4-(4-pyridyl)pyrazole was added dropwise thereto, followed by stirring at room temperature for 30 minutes. Then, 2 ml of a dimethylformamide solution containing 80 mg of methyl iodide was added dropwise thereto, followed by stirring at room temperature for 2 hours. After the dimethylformamide was distilled off under reduced pressure, the resulting residue was purified by column chromatography using 30 g of silica gel [with an elution solvent comprising chloroform-methanol (70:1)]. Thus, 149.2 mg (80% yield) of the title compound was obtained as pale-yellow crystals.

Melting point: 169.8–171.1° C.
$^1$H-NMR (CDCl$_3$) δ: 8.35 (dd, J=1.6, 4.5 Hz, 2H), 7.40–6.90 (m, 9H), 6.67 (dd, J=1.6, 4.5 Hz, 2H), 3.79 (s, 3H), 3.66 (s, 2H), 3.15 (s, 3H)
IR (KBr) ν max: 1658, 1600, 1492, 1354 cm$^{-1}$
Mass, m/e: 400 (M$^+$), 91 (base)

The compounds of the following Examples 120–135 were synthesized in substantially the same manner as in Example 119.

Example 120

3-(4-Fluorophenyl)-1-methyl-5-(N-methyl-N-phenylacetylamino)-4-(4-pyridyl)pyrazole Melting point: 168.5–171.2° C.
$^1$H-NMR (CDCl$_3$) δ: 8.55 (dd, J=1.6, 4.5 Hz, 2H), 7.60–6.75 (m, 11H), 3.35 (s, 2H), 3.31 (s, 3H), 3.23 (s, 3H)
IR (KBr) ν max: 1670, 1600, 1224 cm$^{-1}$
Mass, m/e: 400 (M$^+$), 91 (base)

Example 121

5-[N-(2-chlorophenylacetyl)-N-methylamino]-3-(4-fluorophenyl)-1-methyl-4-(4-pyridyl)pyrazole Melting point: 168.6–171.2° C. (n-hexane-ethyl acetate)
$^1$H-NMR (CDCl$_3$) δ: 8.56 (dd, J=1.5, 4.6 Hz, 2H), 7.53–6.83 (m, 10H), 3.66 (s, 3H), 3.32 (s, 3H), 3.32 (s, 2H)
IR (KBr) ν max: 1680, 1600, 1222 cm$^{-1}$
Mass, m/e: 434 (M$^+$), 125 (base)

Example 122

5-[N-(2,6-dichlorophenylacetyl)-N-methylamino]-3-(4-fluorophenyl)-1-methyl-4-(4-pyridyl)pyrazole Melting point: 205.7–207.8° C. (n-hexane-ethyl acetate)
$^1$H-NMR (CDCl$_3$) δ: 8.56 (dd, J=1.8, 4.7 Hz, 2H), 7.66–6.83 (m, 9H), 3.95 (s, 3H) 3.57 (s, 2H), 3.33 (s, 3H)
IR (KBr) ν max: 1694, 1604, 1440, 1220 cm$^{-1}$
Mass, m/e: 468 (M$^+$), 159 (base)

Example 123

3-(4-Fluorophenyl)-1-methyl-5-[N-methyl-N-(3-pyridylacetyl)amino]-4-(4-pyridyl)pyrazole Melting point: Oily matter
$^1$H-NMR (CDCl$_3$) δ: 8.66–8.30 (m, 3H) 8.13 (bs, 1H), 7.63–6.83 (m, 8H), 3.56 (s, 3H) 3.29 (s, 2H), 3.29 (s, 3H)
IR (KBr) ν max: 1682, 1604, 1220 cm$^{-1}$
Mass, m/e: 401 (M$^+$), 282 (base)

Example 124

3-(4-Fluorophenyl)-1-methyl-5-[N-methyl-N-(4-pyridylacetyl)amino]-4-(4-pyridyl)pyrazole Melting point: Oily matter
$^1$H-NMR (CDCl$_3$) δ: 8.58 (dd, J=1.5, 4.4 Hz, 2H), 8.48 (dd, J=1.5, 4.6 Hz, 2H), 7.53–6.73 (m, 8H), 3.50 (s, 3H), 3.28 (s, 3H), 3.28 (s, 2H)
IR (KBr) ν max: 1680, 1602, 1222 cm$^{-1}$
Mass, m/e: 401 (M$^+$), 92 (base)

Example 125

3-(4-Fluorophenyl)-5-[N-(4-fluorophenylacetyl)-N-methylamino]-1-methyl-4-(4-pyridyl)pyrazole Melting point: 124.1–125.6° C. (n-hexane-ethyl acetate)
$^1$H-NMR (CDCl$_3$) δ: 8.56 (dd, J=1.5, 4.4 Hz, 2H), 7.53–6.73 (m, 10H), 3.43 (s, 3H), 3.28 (s, 2H), 3.25 (s, 3H)
IR (KBr) ν max: 1672, 1604, 1508, 1222 cm$^{-1}$
Mass, m/e: 418 (M$^+$), 109 (base)

Example 126

3-(4-Fluorophenyl)-1-methyl-5-[N-methyl-N-(4-methoxyphenylacetyl)amino]-4-(4-pyridyl)pyrazole Melting point: 175.8–178.1° C. (n-hexane-ethyl acetate)

$^1$H-NMR (CDCl$_3$) δ: 8.54 (dd, J=1.5, 4.4 Hz, 2H), 7.60–6.70 (m, 10H), 3.77 (s, 3H), 3.37 (s, 3H), 3.25 (s, 2H), 3.23 (s, 3H)

IR (KBr) ν max: 1674, 1600, 1510, 1248 cm$^{-1}$

Mass, m/e: 430 (M$^+$), 121 (base)

Example 127

1-Ethyl-3-(4-fluorophenyl)-5-(N-methyl-N-phenylacetylamino)-4-(4-pyridyl)pyrazole Melting point: Oily matter $^1$H-NMR (CDCl$_3$) δ: 8.53 (dd, J=1.5, 4.4 Hz, 2H), 7.56–6.80 (m, 11H), 3.85–3.40 (m, 2H), 3.32 (s, 2H), 3.24 (s, 3H), 1.41 (t, J=7.3 Hz, 3H)

IR (KBr) ν max: 1680, 1600, 1218 cm$^{-1}$

Mass, m/e: 414 (M$^+$), 91 (base)

Example 128

3-(4-Fluorophenyl)-5-(N-methyl-N-phenylacetylamino)-1-propyl-4-(4-pyridyl)pyrazole Melting point: 124.5–127.3° C. (n-hexane-ethyl acetate)

$^1$H-NMR (CDCl$_3$) δ: 8.51 (dd, J=1.5, 4.4 Hz, 2H), 7.55–6.83 (m, 11H), 3.58 (m, 2H), 3.33 (s, 2H), 3.23 (s, 3H), 1.88 (m, 2H), 0.94 (t, J=7.5 Hz, 3H)

IR (KBr) ν max: 1674, 1602, 1496, 1218 cm$^{-1}$

Mass, m/e: 428 (M$^+$), 91 (base)

Example 129

3-(4-Fluorophenyl)-1-methyl-5-[N-methyl-N-(2-pyridylacetyl)amino]-4-(4-pyridyl)pyrazole Melting point: 144.0–145.2° C. (n-hexane-ethyl acetate)

$^1$H-NMR (CDCl$_3$) δ: 8.63–8.40 (m, 1H), 8.55 (dd, J=1.5, 4.4 Hz, 2H), 7.63–6.86 (m, 9H), 3.72 (s, 3H), 3.53 (s, 2H), 3.27 (s, 3H)

IR (KBr) ν max: 1674, 1600, 1224 cm$^{-1}$

Mass, m/e: 401 (M$^+$), 92 (base)

Example 130

3-(4-Fluorophenyl)-5-[N-methyl-N-(2-chlorophenylacetyl)amino]-1-phenyl-4-(4-pyridyl)pyrazole Melting point: 203.8–205.6° C.

$^1$H-NMR (CDCl$_3$) δ: 8.58 (d, J=6.2 Hz, 2H), 7.57–6.74 (m, 15H), 3.41 (s, 2H), 3.18 (s, 3H)

IR (KBr) ν max: 1686, 1604, 1496, 1228, 770 cm$^{-1}$

Mass, m/e: 496 (M$^+$), 344 (base)

Example 131

3-(4-Fluorophenyl)-5-[N-methyl-N-(2-methoxyphenylacetyl)amino]-1-methyl-4-(4-pyridyl)pyrazole Melting point: 143.6–145.3° C.

$^1$H-NMR (CDCl$_3$) δ: 8.55 (br, 2H), 7.50–6.75 (m, 10H), 3.66 (s, 3H), 3.56 (s, 3H), 3.33 (d, J=8.6 Hz, 2H), 3.23 (s, 3H)

IR (KBr) ν max: 2940, 1670, 1608, 1496, 1252, 1228 cm$^{-1}$

Mass, m/e: 430 (M$^+$), 282 (base)

Example 132

3-(4-Fluorophenyl)-1-(2-hydroxyethyl)-5-(N-methyl-N-phenylacetylamino)-4-(4-pyridyl)pyrazole Melting point: Amorphous $^1$H-NMR (CDCl$_3$) δ: 8.56 (dd, J=1.7, 4.6 Hz, 2H), 7.6–6.9 (m, 11H), 4.1–3.4 (m, 4H), 3.32 (s, 2H), 3.26 (s, 3H)

IR (KBr) ν max: 1674, 1608, 842 cm$^{-1}$

Mass, m/e: 430 (M$^+$), 91 (base)

Example 133

5-(N-Acetyl-N-phenetylamino)-3-(4-fluorophenyl)-1-methyl-4-(4-pyridyl)pyrazole

Melting point: Amorphous $^1$H-NMR (CDCl$_3$) δ: 8.57 (dd, J=1.5, 4.4 Hz, 2H), 7.5–6.9 (m, 11H), 4.2–3.2 (m, 2H), 3.66 (s, 3H), 2.9–2.5 (m, 2H), 2.02 (s, 3H)

IR (KBr) ν max: 2852, 1680, 1604, 1448, 1220, 840 cm$^{-1}$

Mass, m/e: 414 (M$^+$), 91 (base)

Example 134

3-(4-Fluorophenyl)-5-(N-formyl-N-phenetylamino)-1-methyl-4-(4-pyridyl)pyrazole

Melting point: Amorphous $^1$H-NMR (CDCl$_3$) δ: 8.58 (dd, J=1.5, 4.4 Hz, 2H), 8.35 (d, J=2.4 Hz, 1H), 7.5–6.8 (m, 11H), 3.9–3.4 (m, 2H), 3.67 (s, 3H), 2.8–2.5 (m, 2H), 2.02 (s, 3H)

IR (KBr) ν max: 1694, 1604, 1450, 1222, 840 cm$^{-1}$

Mass, m/e: 400 (M$^+$), 296 (base)

Example 135

3-(3,4-Dichlorophenyl)-1-methyl-5-(N-methyl-N-phenylacetylamino)-4-(4-pyridyl)pyrazole Melting point: Oily matter $^1$H-NMR (CDCl$_3$) δ: 8.59 (dd, J=1.5, 4.4 Hz, 2H), 7.73–6.76 (m, 10H), 3.30 (s, 3H), 3.30 (s, 2H), 3.23 (s, 3H)

IR (KBr) ν max: 3448, 1682, 1600, 1250 cm$^{-1}$

Mass, m/e: 450 (M$^+$), 91 (base)

Example 136

Synthesis of 3-(4-fluorophenyl)-1-methyl-5-(phenylaminocarbonylamino)-4-(4-pyridyl)pyrazole 150 mg of 5-amino-3-(4-fluorophenyl)-1-methyl-4-(4-pyridyl)pyrazole was dissolved in 5 ml of dichloromethane. Then, 80 mg of phenyl isocyanate and 80 mg of dimethylaminopyridine were added thereto, followed by stirring at room temperature overnight. After the reaction mixture was washed with water and dried over anhydrous magnesium sulfate, the solvent was distilled off under reduced pressure. The resulting residue was purified by column chromatography using 20 g of silica gel and eluted with chloroform-methanol (50:1). Thus, 70 mg of the title compound was obtained and crystallized from ether.

Melting point: 287.5–290.2° C.

$^1$H-NMR (DMSO-d$_6$): 8.46 (dd-like, 2H), 7.55–6.90 (m, 11H), 3.87 (s, 3H)

IR (KBr) ν max: 3320, 1660, 1602, 1212, 181 cm$^{-1}$

Mass, m/e: 387 (M$^+$), 268, 93 (base)

The compound of the following Example 137 was synthesized in substantially the same manner as in Example 136.

Example 137

5-(2,3-Dichlorophenylaminocarbonylamino)-3-(4-fluorophenyl)-1-methyl-4-(4-pyridyl)pyrazole Melting point: 300° C. or above $^1$H-NMR (DMSO-d$_6$): 13.2 (bs, 1H), 9.1 (bs, 2H), 8.52 (d-like, 2H), 8.08 (m, 1H), 7.45–7.1 (m, 8H)

IR (KBr) ν max: 3340, 1660, 1220 cm$^{-1}$

Mass, m/e: 441 (M$^+$), 280, 161 (base)

Example 138

Synthesis of 5-(4-fluorophenyl)-4-(4-pyridyl)-3-thiopropionylamino-pyrazole 175 mg of 5-(4-fluorophenyl)-3-propionylamino-4-(4-pyridyl)pyrazole and 450 mg of 2,4-bis(4-methoxyphenyl)-1,3-dithia-2,4-diphosphetane-2,4-disulfide were added to 30 ml of toluene, followed by heating under reflux for 2 hours. After the reaction mixture was cooled, 10% hydrochloric acid and ethyl acetate were added thereto. The aqueous layer was separated, neutralized with a saturation solution of sodium hydrogen carbonate, and extracted with chloroform-methanol (5:1). After the organic layer was dried over anhydrous magnesium sulfate, the solvent was distilled off under reduced pressure. The resulting residue was purified by silica gel thin-layer chromatography (using chloroform-methanol (10:1) as the developing solvent). Thus, 113 mg (61% yield) of the title compound was obtained as pale-yellow crystals.

$^1$H-NMR (DMSO-d$_6$) δ: 13.40 (bs, 1H), 11.28 (bs, 1H), 8.45 (d, J=5.7 Hz, 2H), 7.50–7.20 (m, 4H), 7.12 (dd, J=1.4, 4.7 Hz, 2H), 2.71–2.41 (m, 2H), 1.19 (t, J=7.2 Hz, 3H)

IR (KBr) ν max: 1598, 1510, 1236, 838 cm$^{-1}$

Mass, m/e: 326 (M$^+$), 254, 73 (base)

Example 139

Synthesis of 5-(4-fluorophenyl)-3-phenylsulfonylamino-4-(4-pyridyl)pyrazole

Under a stream of argon gas, 333 mg of benzenesulfonyl chloride was added dropwise to 4 ml of a tetrahydrofuran solution containing 150 mg of 3-amino-5-(4-fluorophenyl)-4-(4-pyridyl)pyrazole and 191 mg of triethylamine, followed by stirring at room temperature for 1.5 hours. After the reaction mixture was concentrated under reduced pressure, the resulting residue was purified by column chromatography using 20 g of silica gel [with an elution solvent comprising chloroform-methanol (100:1)]. Thus, 35 mg (15% yield) of the title compound was obtained as a pale-yellow powder.

Melting point: 181.0–183.3° C.

$^1$H-NMR, m) δ: 8.43 (dd, J=1.5, 4.4 Hz, 2H), 7.69–7.06 (m, 9H), 6.97 (dd, J=1.6, 4.4 Hz, 2H)

IR (KBr) ν max: 3320, 1602, 1528, 1450, 1384 cm$^{-1}$

Mass, m/e: 394 (M$^+$), 225 (base)

The compound of the following Example 140 was synthesized in substantially the same manner as in Example 139.

Example 140

5-(4-Fluorophenyl)-4-(4-pyridyl)-3-(p-toluenesulfonylamino)pyrazole

Melting point: 221.2–221.5° C.

$^1$H-NMR (CDCl$_3$) δ: 8.45 (dd, J=1.5, 4.4 Hz, 2H), 7.58–7.03 (m, 8H), 6.96 (dd, J=1.5, 4.4 Hz, 2H), 2.41 (s, 3H)

IR (KBr) ν max: 3316, 1602, 1524, 1446, 1382 cm$^{-1}$

Mass, m/e: 408 (M$^+$), 225 (base)

Next, an example of a pharmaceutical preparation containing a compound in accordance with the present invention is given.

Preparation Example A: Tablets

| Tablets: | |
|---|---|
|  | mg/tablet |
| Active ingredient | 10.0 |
| Starch | 15.0 |
| Lactose | 127.0 |
| Carboxymethylcellulose calcium | 15.0 |
| Talc | 2.0 |
| Magnesium stearate | 1.0 |
|  | 170.0 |

The active ingredient is pulverized to a particle size of 70 microns or less. Then, starch, lactose and carboxymethylcellulose calcium are added thereto and thoroughly mixed therewith. After the addition of 10% starch paste, the above powder mixture is agitated and blended to prepare granules. After drying, these granules are adjusted to a particle diameter of about 1,000 microns, and mixed with talc and magnesium stearate. The resulting mixture is formed into tablets.

What is claimed is:

1. An aminopyrazole derivative represented by the following formula, or a salt thereof:

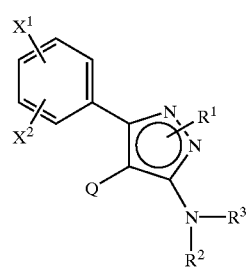

(I)

wherein:
  X$^1$ and X$^2$ each independently represent a hydrogen atom or a halogen atom, or when X$^1$ and X$^2$ are attached to positions adjacent to each other, they may be united together to form a lower alkylenedioxy group;
  Q represents a pyridyl group or a quinolyl group;
  R$^1$ represents a hydrogen atom, a substituted or unsubstituted lower alkyl group, or a substituted or unsubstituted aryl group;
  R$^2$ represents a hydrogen atom, a lower alkyl group, or an aralkyl group in which the aryl moiety may optionally be substituted;
  R$^3$ represents —C(=Y)—R$^4$ in which R$^4$ is a hydrogen atom or an organic residue and Y is an oxygen atom.

2. An aminopyrazole derivative or a salt thereof as claimed in claim 1 wherein $X^1$ is a 4-fluoro radical and $X^2$ is a hydrogen atom.

3. An aminopyrazole derivative or a salt thereof as claimed in claim 1 wherein Q is a 4-pyridyl group.

4. An aminopyrazole derivative or a salt thereof as claimed in claim 1 wherein $R^1$ is an unsubstituted lower alkyl group.

5. An aminopyrazole derivative or a salt thereof as claimed in claim 1 wherein $R^2$ is a hydrogen atom or a methyl group.

6. An aminopyrazole derivative or a salt thereof as claimed in claim 1 wherein the organic residue represented by $R^4$ is a substituted or unsubstituted, saturated or unsaturated straight-chain, branched or cyclic hydrocarbon radical, a substituted or unsubstituted heterocyclic group, a substituted or unsubstituted amino group, or a substituted carbonyl group.

7. An aminopyrazole derivative or a salt thereof as claimed in claim 6 wherein the substituted or unsubstituted, saturated or unsaturated straight-chain, branched or cyclic hydrocarbon radical represented by $R^4$ is a substituted or unsubstituted alkyl group, a substituted or unsubstituted alkenyl group, a substituted or unsubstituted alkynyl group, a substituted or unsubstituted cycloalkyl group, a substituted or unsubstituted cycloalkenyl group, a substituted or unsubstituted aryl group, a substituted or unsubstituted, bridged cycloalkyl group, or a substituted or unsubstituted spiroalkyl group.

8. An aminopyrazole derivative or a salt thereof as claimed in claim 6 wherein the heterocyclic group in the substituted or unsubstituted heterocyclic group represented by $R^4$ is a monocyclic or polycyclic heterocycle which contains 1 to 4 heteroatoms selected from N, O and S and has a four- to eight-membered ring, and the heterocycle may further be fused with a cyclic hydrocarbon radical.

9. An aminopyrazole derivative or a salt thereof as claimed in claim 6 wherein the substituted or unsubstituted amino group represented by $R^4$ is a lower alkylamino group, a di(lower alkyl)amino group, or a substituted or unsubstituted arylamino group.

10. An aminopyrazole derivative or a salt thereof as claimed in claim 6 wherein the substituted carbonyl group represented by $R^4$ is a substituted or unsubstituted alkyloxycarbonyl group, a substituted or unsubstituted alkylcarbonyl group, or a substituted or unsubstituted arylcarbonyl group.

11. An aminopyrazole derivative or a salt thereof as claimed in claim 6 wherein the organic residue represented by $R^4$ is a substituted or unsubstituted alkyl group, a substituted or unsubstituted alkenyl group, a substituted or unsubstituted cycloalkyl group, or a substituted or unsubstituted aryl group; a substituted or unsubstituted, monocyclic or bicyclic heterocyclic group which contains 1 or 2 heteroatoms selected from N, O and S and has a five- or six-membered ring, and which may further be fused with a phenyl group; a substituted or unsubstituted arylamino group; or a substituted or unsubstituted lower alkyloxycarbonyl group or a substituted or unsubstituted phenylcarbonyl group.

12. An aminopyrazole derivative or a salt thereof as claimed in claim 11 wherein the organic residue represented by $R^4$ is:

an alkyl group which may optionally be substituted by 1 to 3 substituents selected from halogen, hydroxyl, lower alkoxy, lower alkanoyloxy, arylcarbonyloxy, aryloxy, mercapto, lower alkylthio, lower alkanoylthio, arylcarbonylthio, arylthio, amino, lower alkylamino, di(lower alkyl)amino, lower alkanoylamino, arylcarbonylamino, aralkyloxycarbonylamino, lower alkoxycarbonylamino, N-(lower alkyl)-N-(lower alkoxycarbonyl)amino, guanidino, carboxyl, lower alkoxycarbonyl, aralkyloxycarbonyl, carbamoyl, lower alkylcarbonyl, arylcarbonyl, cycloalkyl; aryl which may optionally be substituted by 1 to 5 substituents selected from halogen, lower alkyl, halogeno(lower alkyl), lower alkoxy, lower alkylenedioxy, hydroxyl, aralkyloxy, lower alkanoyloxy, mercapto, lower alkylthio, amino, lower alkylamino, di(lower alkyl) amino, lower alkanoylamino, aralkyloxycarbonylamino, lower alkoxycarbonylamino and nitro; and a monocyclic or bicyclic heteroyclic group which contains 1 or 2 heteroatoms selected from N, O and S and has a five- or six-membered ring and which may further be fused with a benzene ring which heterocyclic group may optionally be substituted by 1 or 2 substituents selected from halogen, lower alkyl, lower alkoxy and nitro;

an alkenyl group which may optionally be substituted by 1 or 2 substituents selected from halogen and aryl which aryl may optionally be substituted by 1 to 5 substituents selected from halogen, lower alkyl, halogeno(lower alkyl), lower alkoxy, lower alkylenedioxy, hydroxyl, aralkyloxy, lower alkanoyloxy, mercapto, lower alkylthio, amino, lower alkylamino, di(lower alkyl)amino, lower alkanoylamino, aralkyloxycarbonylamino, lower alkoxycarbonylamino and nitro;

a cycloalkyl group which may optionally be substituted by 1 or 2 substituents selected from lower alkyl, hydroxyl, lower alkoxy, lower alkanoyloxy, carboxyl, lower alkoxycarbonyl and oxo; or an aryl group which may optionally be substituted by 1 to 5 substituents selected from halogen, lower alkyl, lower alkoxy, lower alkylenedioxy, hydroxyl, aralkyloxy, lower alkanoyloxy, mercapto, lower alkylthio, amino, lower alkylamino, di(lower alkyl)amino, lower alkanoylamino and nitro.

13. An aminopyrazole derivative or a salt thereof as claimed in claim 11 wherein the substituted or unsubstituted alkyl group represented by $R^4$ is a lower alkyl group which may optionally be substituted by 1 or 2 substituents selected from halogen, hydroxyl, lower alkoxy, lower alkanoyloxy, aryloxy, amino, lower alkylamino, di(lower alkyl)amino, aralkyloxycarbonylamino, lower alkoxycarbonylamino, N-(lower alkyl)-N-(lower alkoxycarbonyl)amino, carboxyl, lower alkoxycarbonyl, lower cycloalkyl; aryl which may optionally be substituted by 1 to 5 halogen atoms or 1 to 3 substituents selected from lower alkyl, halogeno(lower alkyl), lower alkoxy, lower alkylenedioxy, hydroxyl, aralkyloxy, lower alkanoyloxy, mercapto, lower alkylthio, amino, lower alkoxycarbonylamino and nitro; and a monocyclic or bicyclic heteroaryl group which contains 1 or 2 heteroatoms selected from N and S and has a five- or six-membered ring and which may further be fused with a benzene ring which heteroaryl group may optionally be substituted by one lower alkyl group.

14. An aminopyrazole derivative or a salt thereof as claimed in claim 11 wherein the substituted or unsubstituted alkyl group represented by $R^4$ is a lower alkyl group substituted by an aryl group which aryl group may optionally be substituted by 1 to 5 halogen atoms or 1 to 3 substituents selected from lower alkyl, halogeno(lower alkyl), lower alkoxy, lower alkylenedioxy, hydroxyl, aralkyloxy, lower alkylthio, amino and nitro, or substituted by a five- or six-membered heteroaryl group containing 1 or 2 heteroatoms selected from N and S which heteroaryl group may optionally be substituted by one lower alkyl group.

15. An aminopyrazole derivative or a salt thereof as claimed in claim 11 wherein the substituted or unsubstituted alkenyl group, the substituted or unsubstituted cycloalkyl group, and the substituted or unsubstituted aryl group, all represented by $R^4$, are an unsubstituted alkenyl group of 2 to 4 carbon atoms, an unsubstituted cycloalkyl group of 5 to 7 carbon atoms, and an unsubstituted aryl group of 6 to 10 carbon atoms, respectively.

16. An aminopyrazole derivative or a salt thereof as claimed in claim 6 wherein the substituted or unsubstituted heterocyclic group represented by $R^4$ is a heterocyclic group which may optionally be substituted by 1 to 3 substituents selected from halogen, lower alkyl lower alkoxy, lower alkylenedioxy, hydroxyl lower alkanoyloxy, amino, lower alkylamino, di(lower alkyl)amino, lower alkanoylamino, aralkyloxycarbonyl lower alkoxycarbonyl and nitro.

17. An aminopyrazole derivative or a salt thereof as claimed in claim 6 wherein the substituted or unsubstituted heterocyclic group represented by $R^4$ is a monocyclic or bicyclic heterocyclic group which contains 1 or 2 heteroatoms selected from N and O and has a five- or six-membered ring, which may farther be fused with a benzene ring, and which may optionally be substituted by one aralkyloxycarbonyl or lower alkoxycarbonyl group.

18. An aminopyrazole derivative or a salt thereof as claimed in claim 11 wherein the substituted or unsubstituted arylamino group represented by $R^4$ is an arylamino group in which the aryl moiety may optionally be substituted by 1 to 5 halogen atoms or 1 to 3 substituents selected from lower alkyl halogeno(lower alkyl), lower alkoxy, lower alkylenedioxy, hydroxyl aralkyloxy, lower alkylthio, amino and nitro.

19. An aminopyrazole derivative or a salt thereof as claimed in claim 11 wherein the substituted or unsubstituted lower alkyloxycarbonyl group and the substituted or unsubstituted phenylcarbonyl group, both represented by $R^4$, are, respectively:

a lower alkyloxycarbonyl group which may optionally be substituted by 1 or 2 substituents selected from hydroxyl, lower alkoxy, amino, lower alkylamino and aryl which aryl may optionally be substituted by 1 to 5 substituents selected from halogen, lower alkyl, halogeno(lower alkyl), lower alkoxy, lower alkylenedioxy, hydroxyl, aralkyloxy, lower alkanoyloxy, mercapto, lower alkylthio, amino, lower alkoxycarbonylamino and nitro; and a phenylcarbonyl group which may optionally be substituted by 1 to 3 substituents selected from halogen, lower alkyl, lower alkoxy, amino, lower alkoxycarbonylamino and nitro.

20. An aminopyrazole derivative or a salt thereof as claimed in claim 11 wherein the substituted or unsubstituted lower alkyloxycarbonyl group and the substituted or unsubstituted phenylcarbonyl group, both represented by $R^4$, are an unsubstituted lower alkoxycarbonyl group and an unsubstituted phenylcarbonyl group, respectively.

21. A pharmaceutical composition comprising an aminopyrazole derivative of formula (I) or a salt thereof as claimed in claim 1 and a pharmaceutically acceptable additive.

22. A method for treatment of a disease associated with tumor necrosis factor α, interleukin 1, interleukin 6 or cyclooxygenase II in a human being or other mammal, which comprises administering an effective amount of an aminopyrazole derivative of formula (I) or a salt thereof as claimed in claim 1, to the human being or other mammal.

23. The method as claimed in claim 22, wherein the disease is IBD.

* * * * *